(12) United States Patent
Espensen et al.

(10) Patent No.: US 10,065,954 B2
(45) Date of Patent: Sep. 4, 2018

(54) SUBSTITUTED IMIDAZO[4,5-C]PYRIDINES AS SSAO INHIBITORS

(71) Applicant: Proximagen Limited, Cambridge (GB)

(72) Inventors: Max Espensen, London (GB); Lee Patient, Linton (GB); Edward Savory, Cambourne (GB)

(73) Assignee: PROXIMAGEN LIMITED, Cambridge (GB)

( * ) Notice: Subject to any disclaimer, the term of this patent is extended or adjusted under 35 U.S.C. 154(b) by 0 days.

(21) Appl. No.: 15/506,885

(22) PCT Filed: Sep. 17, 2015

(86) PCT No.: PCT/GB2015/052690
§ 371 (c)(1),
(2) Date: Feb. 27, 2017

(87) PCT Pub. No.: WO2016/042331
PCT Pub. Date: Mar. 24, 2016

(65) Prior Publication Data
US 2017/0362218 A1    Dec. 21, 2017

(30) Foreign Application Priority Data
Sep. 17, 2014 (GB) .................................. 1416446.1

(51) Int. Cl.
*A61K 31/437* (2006.01)
*C07D 471/04* (2006.01)

(52) U.S. Cl.
CPC .................................. *C07D 471/04* (2013.01)

(58) Field of Classification Search
CPC .......................... A61K 31/437; C07D 471/04
USPC .......................................... 514/303; 546/118
See application file for complete search history.

(56) References Cited

U.S. PATENT DOCUMENTS

| | | | |
|---|---|---|---|
| 7,405,300 B2 | 7/2008 | Jiang et al. | |
| 9,428,498 B2 | 8/2016 | Espensen et al. | |
| 9,580,415 B2 | 2/2017 | Patient et al. | |
| 2005/0054631 A1 | 3/2005 | Jiang et al. | |
| 2014/0275040 A1 | 9/2014 | Espensen et al. | |
| 2015/0258101 A1 | 9/2015 | Espensen et al. | |
| 2016/0024080 A1 | 1/2016 | Patient et al. | |
| 2016/0046622 A1 | 2/2016 | Espensen et al. | |
| 2016/0326172 A1 | 11/2016 | Espensen et al. | |

FOREIGN PATENT DOCUMENTS

| | | | |
|---|---|---|---|
| WO | 2002038153 A1 | 5/2002 | |
| WO | 2003006003 A1 | 1/2003 | |
| WO | 2005014530 A | 2/2005 | |
| WO | 2007120528 A2 | 10/2007 | |
| WO | 2010031789 A1 | 3/2010 | |
| WO | 2010031791 A1 | 3/2010 | |
| WO | 2010064020 A1 | 6/2010 | |
| WO | 2010117935 A1 | 10/2010 | |
| WO | 2011113798 A2 | 9/2011 | |
| WO | 2012/146667 A1 | 11/2012 | |
| WO | 2013037411 A1 | 3/2013 | |
| WO | 2013038189 A1 | 3/2013 | |
| WO | 2013078254 A1 | 5/2013 | |
| WO | 2014140591 A1 | 9/2014 | |
| WO | 2014140592 A1 | 9/2014 | |
| WO | 2015189534 A1 | 12/2015 | |
| WO | 2016042332 A1 | 3/2016 | |
| WO | WO 16/042331 | * | 3/2016 |

OTHER PUBLICATIONS

Jordan, V. C. Nature Reviews: Drug Discovery, 2, 2003, 205.*
Hackam, et al. JAMA, 296(14), 2006, 1731-1732.*
CAS Registry No. 340159-15-1, Jun. 8, 2001, Compound 2-(2,3-dihydro-1,3-dimethyl-1H-benzimidazol-2-yl)-3-phenyl-3H-imidazo[4,5-c]pyridine.
Database Registry [online], Chemical Abstracts Service, Columbus, Ohio, US; Jan. 19, 2011, XP002723294, database accession No. 1259952-23-2 abstract.
Dunkel, Petra et al. "Semicarbazide-sensitive amine oxidase/vascular adhesion protein-1: a patent survey," Expert Opin. Ther. Patents, 21(9): 1453-1471 (2011).
International Search Report dated Dec. 15, 2015 for PCT application No. PCT/GB2015/052690 filed Sep. 17, 2015.
International Search Report dated Dec. 15, 2015 for PCT application No. PCT/GB2015/052691 filed Sep. 17, 2015.

(Continued)

*Primary Examiner* — Douglas M Willis
(74) *Attorney, Agent, or Firm* — Greenblum & Bernstein, P.L.C.

(57) ABSTRACT

Specific compounds of formula (Ia):

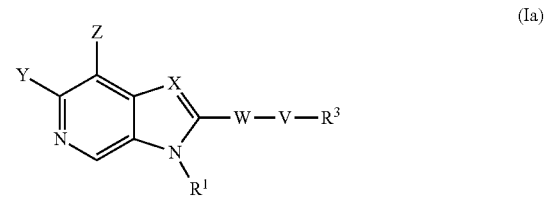

and pharmaceutically acceptable salts thereof. Pharmaceutical compositions of the specific compounds of formula (Ia) and pharmaceutically acceptable salts thereof. A method for inhibiting tumor growth in a subject that includes administering to the subject an effective amount of a compound selected from the specific compounds of formula (Ia) and pharmaceutically acceptable salts thereof. A method for modulating semicarbazide-sensitive amine oxidase activity in a subject that includes administering to the subject an effective amount of a compound selected from the specific compounds of formula (Ia) and pharmaceutically acceptable salts thereof.

17 Claims, No Drawings

(56) References Cited

OTHER PUBLICATIONS

Melkonyan, Ferdinand S., et al. "One-pot synthesis of substituted indoles via titanium(iv) alkoxide mediated imine formation—copper-catalyzed N-arylation," RSC Advances, vol. 3, No. 22, Mar. 21, 2013, p. 8388, XP055113497.
UKIPO Search Report dated Jan. 13, 2016 for GB Application No. 1416444.6 filed on Sep. 17, 2014.
Wilson, Robert J., et al. "Copper- and Palladium-Catalyzed Amidation Reactions for the Synthesis of Substituted Imidazo[4,5-c]pyridines," The Journal of Organic Chemistry, vol. 79, No. 5, Feb. 6, 2014, pp. 2203-2212, XP055113503.
Hackam et al., "Translation of Research Evidence from Animals to Humans", JAMA, 2006, 296(14), pp. 1731-1732.
Jordan, "Tamoxifen: A Most Unlikely Pioneering Medicine", Nature Reviews: Drug Discovery, 2003, vol. 2, pp. 205-213.
UKIPO Search Report from GB 13045273 dated Aug. 28, 2013.
International Search Report for PCT/GB2014/050765 dated May 8, 2014.
International Search Report for PCT/GB2014/050764 dated Apr. 28, 2014.
UKIPO Search Report from GB 1304526.5 dated Aug. 21, 2013.

\* cited by examiner

SUBSTITUTED IMIDAZO[4,5-C]PYRIDINES AS SSAO INHIBITORS

This application is a 371 national stage application of international patent application no. PCT/GB2015/052690 filed on Sep. 17, 2015, which claims priority to United Kingdom application number 1416446.1 filed on Sep. 17, 2014. The above applications are incorporated herein by reference in their entirety.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

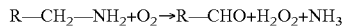

$$R\text{---}CH_2\text{---}NH_2 + O_2 \rightarrow R\text{---}CHO + H_2O_2 + NH_3$$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61 (Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

WO2007146188 teaches that blocking SSAO activity inhibits leucocyte recruitment, reduces the inflammatory response, and is expected to be beneficial in prevention and treatment of seizures, for example, in epilepsy.

O'Rourke et al (*J Neural Transm.* 2007; 114(6):845-9) examined the potential of SSAO inhibitors in neurological diseases, having previously demonstrated the efficacy of SSAO inhibition in a rat model of stroke. An SSAO inhibitor is tested on relapsing-remitting experimental autoimmune encephalomyelitis (EAE), a mouse model that shares many characteristics with human multiple sclerosis. The data demonstrates the potential clinical benefit of small molecule anti-SSAO therapy in this model and therefore in treatment of human multiple sclerosis.

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. VAP-1 has also been implicated in the progression and maintenance of fibrotic diseases including those of the liver and lung. Weston and Adams (J Neural Transm. 2011, 118(7), 1055-64) have summarised the experimental data implicating VAP-1 in liver fibrosis, and Weston et al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88.; Irjala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40.). One report (Marttila-lchihara F, Castermans K, Auvinen K, Oude Egbrink M G, Jalkanen S, Griffioen A W, Salmi M. (2010), J Immunol. 184, 3164-3173.) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in WO2013/037411 and WO2013/038189.

Patent application PCT/US2012/066153 (published as WO2013/078254) discloses compounds apparently useful as inhibitors of serine/threonine protein kinases. The compounds are structurally related to the claimed compounds, and have a bicyclic heteroaryl ring system substituted with a phenyl-cyclobutaneamine substituent.

The invention described here relates to a new class of SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

Our co-pending International Patent Application No. PCT/GB2014/050765 relates to SSAO inhibitors of formula (I) or a pharmaceutically acceptable salt, or N-oxide thereof:

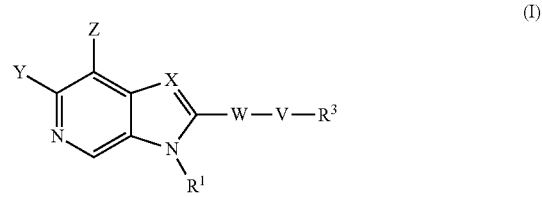

(I)

Wherein:

Y is selected from hydrogen, hydroxyl, $-NH_2$, $-NH-C_{1-4}$-alkyl, $-NH$-halo-$C_{1-4}$-alkyl, or $-C_{1-4}$-alkoxy;

Z is selected from hydrogen, halogen, hydroxyl, cyano, $C_{1-4}$-alkyl, halo-$C_{1-4}$-alkyl, $C_{1-4}$-alkoxy, halo-$C_{1-4}$-alkoxy, $-CONH_2$, $-SO_2NH_2$, $-NH_2$, $-NHC_{1-4}$-alkyl, or $-NH$halo-$C_{1-4}$-alkyl;

$R^1$ is a phenyl ring, or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, a 3-7 membered cycloalkyl ring, $-OR^5$, $-NR^6C(O)OR^5$, $-NR^6C(O)R^5$, $-NR^6C(O)NR^{4A}R^{4B}$, $-C(O)NR^{4A}R^{4B}$, $-C(O)R^5$, $-C(O)OR^5$, and $-NR^6S(O)_2R^5$; wherein $R^{4A}$, $R^{4B}$ $R^5$ and $R^6$ are each independently selected from hydrogen, $C_{1-4}$-alkyl or halo-$C_{1-4}$-alkyl, or $R^{4A}$ and $R^{4B}$ together with the nitrogen to which they are attached form a 3-7 membered cyclic amino group, optionally substituted by one or more substituents selected from: halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, —NHhalo-$C_{1-4}$-alkyl;

X is —N═;

W is a phenyl ring or a 5 or 6-membered heteroaryl ring selected from pyridinyl, pyridazinyl, pyrazinyl, pyrimidinyl, oxazolyl, thiazolyl or imidazolyl, any of which rings being optionally substituted with one or more substituents selected from halogen, cyano, oxo, $C_{1-4}$-alkyl, halo-$C_{1-4}$-alkyl, cyano-$C_{1-4}$-alkyl, —$OR^5$, —$NR^{7A}R^{7B}$, —$NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$;

$R^{7A}$ and $R^{7B}$ are independently hydrogen, $C_{1-4}$-alkyl or halo-$C_{1-4}$-alkyl.

V is selected from a bond, —O—, —$N(R^6)$—, —(C═O)—, —$CONR^6$—, —$NR^6C(O)$—, or —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —$N(R^6)$—;

$R^3$ is selected from hydrogen, —$C_{1-4}$-alkyl, —$C_{1-4}$-alkyl-$C_{1-4}$-alkoxy or a 3-7 membered heterocyclic ring or 3-7 membered cycloalkyl ring, or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —$NR^{4A}R^{4B}$, —$NR^6C(O)OR^6$, —$NR^6C(O)R^6$, —$NR^6C(O)NR^{4A}R^{4B}$, —$C(O)NR^{4A}R^{4B}$, —$C(O)R^5$, —$C(O)OR^6$, —$SO_2R^6$, —$SO_2NR^{4A}R^{4B}$ and —$NR^6S(O)_2R^5$;

PROVIDED THAT groups VWR³ and/or R¹ are not:

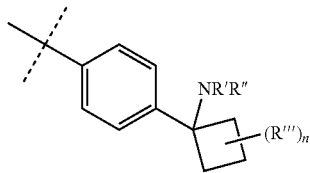

wherein
n is 0, 1, or 2;
R' and R" are independently selected from the group consisting of H, —$C_1$-$C_6$alkyl, —(C═O)—$C_1$-$C_6$ alkyl and —(C═O)OC(CH_3)_3; and
R''' is H, OH, or $C_1$-$C_6$ alkyl.

Our co-pending International Patent Application No. PCT/GB2014/050765 relates also to SSAO inhibitors of formula (Ia) or a pharmaceutically acceptable salt, or N-oxide thereof:

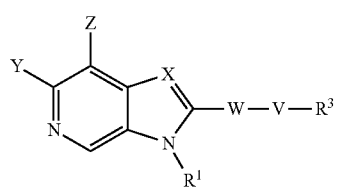

(Ia)

Wherein:
Y is selected from hydrogen, hydroxyl, —$NH_2$, —NH—$C_{1-4}$-alkyl, —NH-halo-$C_{1-4}$-alkyl, or —$C_{1-4}$-alkoxy;

Z is selected from hydrogen, halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, or —NHhalo-$C_{1-4}$-alkyl;

$R^1$ is a phenyl ring, or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, and —$NR^6S(O)_2R^5$; wherein $R^{4A}$, $R^{4B}$ $R^5$ and $R^6$ are each independently selected from hydrogen, $C_{1-4}$-alkyl or halo-$C_{1-4}$-alkyl, or $R^{4A}$ and $R^{4B}$ together with the nitrogen to which they are attached form a 3-7 membered cyclic amino group, optionally substituted by one or more substituents selected from: halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, —NHhalo-$C_{1-4}$-alkyl;

X is —N═;

W is a phenyl ring or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^{7A}R^{7B}$, —$NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$;

$R^{7A}$ and $R^{7B}$ are independently hydrogen, $C_{1-4}$-alkyl or halo-$C_{1-4}$-alkyl.

V is selected from a bond, —O—, —$N(R^6)$—, —(C═O)—, —$CONR^6$—, —$NR^6C(O)$—, or —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —$N(R^6)$—;

$R^3$ is hydrogen, or a 3-7 membered heterocyclic ring, or 3-7 membered cycloalkyl ring selected from cyclopropyl, cyclopentyl or cyclohexyl, or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$.

BRIEF DESCRIPTION OF THE INVENTION

The present invention relates to a group of specific compounds falling within the general disclosure of PCT/GB2014/050765, but not specifically exemplified therein. The present compounds have the utilities disclosed herein.

DETAILED DESCRIPTION OF THE INVENTION

According to the invention there is provided a compound selected from the group consisting of:
4-{5-[3-(5-Fluoropyridin-2-yl)-3H-imidazo[4,5-c]pyridin-2-yl]pyridin-2-yl}morpholine;
4-{5-[3-(2,4-Difluorophenyl)-3H-imidazo[4,5-c]pyridin-2-yl]-4-methylpyridin-2-yl}morpholine;
5-[3-(2,4-Difluorophenyl)-3H-imidazo[4,5-c]pyridin-2-yl]-N-(oxan-4-yl)pyrimidin-2-amine;

N,N-Diethyl-5-[3-(6-methylpyridin-3-yl)-3H-imidazo[4,5-c]pyridin-2-yl]pyrimidin-2-amine;
N,N-Diethyl-5-[3-(4-fluorophenyl)-3H-imidazo[4,5-c]pyridin-2-yl]pyrimidin-2-amine;
N,N-Diethyl-5-[3-(4-methylphenyl)-3H-imidazo[4,5-c]pyridin-2-yl]pyrimidin-2-amine;
N,N-Diethyl-5-[3-(5-methylpyridin-2-yl)-3H-imidazo[4,5-c]pyridin-2-yl]pyrimidin-2-amine;
4-{5-[3-(2-Fluoro-4-methylphenyl)-3H-imidazo[4,5-c]pyridin-2-yl]-4-methylpyridin-2-yl}morpholine;
4-{5-[3-(4-Chlorophenyl)-3H-imidazo[4,5-c]pyridin-2-yl]-4-methylpyridin-2-yl}morpholine;
5-[3-(4-Methylphenyl)-3H-imidazo[4,5-c]pyridin-2-yl]-N-(oxan-4-yl)pyridin-2-amine;
2-(4,4-Difluoropiperidin-1-yl)-5-[3-(4-methylphenyl)-3H-imidazo[4,5-c]pyridin-2-yl]pyridine;
4-{5-[3-(5-Chloropyridin-2-yl)-3H-imidazo[4,5-c]pyridin-2-yl]-4-methylpyridin-2-yl}morpholine;
4-{4-Methyl-5-[3-(5-methylpyridin-2-yl)-3H-imidazo[4,5-c]pyridin-2-yl]pyridin-2-yl}morpholine;
4-{5-[3-(5-Fluoropyridin-2-yl)-3H-imidazo[4,5-c]pyridin-2-yl]-4-methylpyridin-2-yl}morpholine;
5-[3-(4-Fluorophenyl)-3H-imidazo[4,5-c]pyridin-2-yl]-N-(oxan-4-yl)pyridin-2-amine;
4-{5-[3-(4-Fluorophenyl)-3H-imidazo[4,5-c]pyridin-2-yl]pyridin-2-yl}thiomorpholine;
N-Cyclopropyl-5-[3-(4-methylphenyl)-3H-imidazo[4,5-c]pyridin-2-yl]pyridin-2-amine;
5-[3-(6-Methylpyridin-3-yl)-3H-imidazo[4,5-c]pyridin-2-yl]-2-(pyrrolidin-1-yl)pyridine;
2-(4-Fluoropiperidin-1-yl)-5-[3-(6-methylpyridin-3-yl)-3H-imidazo[4,5-c]pyridin-2-yl]pyridine;
5-[3-(4-Fluorophenyl)-3H-imidazo[4,5-c]pyridin-2-yl]-N-[2-(morpholin-4-yl)ethyl]pyridin-2-amine;
5-[3-(4-Methylphenyl)-3H-imidazo[4,5-c]pyridin-2-yl]-N-[2-(morpholin-4-yl)ethyl]pyridin-2-amine;
N-Cyclopropyl-5-[3-(4-fluorophenyl)-3H-imidazo[4,5-c]pyridin-2-yl]pyridin-2-amine;
N-Cyclopropyl-5-[3-(6-methylpyridin-3-yl)-3H-imidazo[4,5-c]pyridin-2-yl]pyridin-2-amine;
5-[3-(4-Methylphenyl)-3H-imidazo[4,5-c]pyridin-2-yl]-N-(propan-2-yl)pyridin-2-amine
5-[3-(6-Methylpyridin-3-yl)-3H-imidazo[4,5-c]pyridin-2-yl]-2-(pyrrolidin-1-yl)pyrimidine;
5-[3-(5-Methylpyridin-2-yl)-3H-imidazo[4,5-c]pyridin-2-yl]-2-(pyrrolidin-1-yl)pyrimidine;
5-[3-(5-Fluoropyridin-2-yl)-3H-imidazo[4,5-c]pyridin-2-yl]-2-(pyrrolidin-1-yl)pyrimidine;
4-{4-[3-(6-Methylpyridin-3-yl)-3H-imidazo[4,5-c]pyridin-2-yl]phenyl}morpholine;
5-[3-(4-Methylphenyl)-3H-imidazo[4,5-c]pyridin-2-yl]-2-(pyrrolidin-1-yl)pyrimidine;
4-{4-[3-(5-Methylpyridin-2-yl)-3H-imidazo[4,5-c]pyridin-2-yl]phenyl}morpholine;
2-Methyl-5-{2-[4-(pyrrolidin-1-yl)phenyl]-3H-imidazo[4,5-c]pyridin-3-yl}pyridine;
5-{2-[2-Fluoro-4-(pyrrolidin-1-yl)phenyl]-3H-imidazo[4,5-c]pyridin-3-yl}-2-methylpyridine;
4-{3-Fluoro-4-[3-(6-methylpyridin-3-yl)-3H-imidazo[4,5-c]pyridin-2-yl]phenyl}morpholine;
5-{2-[3-Fluoro-4-(pyrrolidin-1-yl)phenyl]-3H-imidazo[4,5-c]pyridin-3-yl}-2-methylpyridine;
N-{4-[3-(6-Methylpyridin-3-yl)-3H-imidazo[4,5-c]pyridin-2-yl]phenyl}oxan-4-amine;
5-Methyl-2-{2-[4-(pyrrolidin-1-yl)phenyl]-3H-imidazo[4,5-c]pyridin-3-yl}pyridine;
5-{2-[4-(4-Fluoropiperidin-1-yl)phenyl]-3H-imidazo[4,5-c]pyridin-3-yl}-2-methylpyridine;
2-Chloro-5-[3-(4-chlorophenyl)-3H-imidazo[4,5-c]pyridin-2-yl]pyridine
2-Chloro-5-[3-(4-fluorophenyl)-3H-imidazo[4,5-c]pyridin-2-yl]pyridine
and pharmaceutically acceptable salts thereof.

It is expected that compounds of the invention may be prepared in the form of hydrates, and solvates. Any reference herein, including the claims herein, to "compounds with which the invention is concerned" or "compounds of the invention" or "the present compounds", and the like, includes reference to salts, hydrates, and solvates of such compounds. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Individual compounds of the invention may exist in an amorphous form and/or several polymorphic forms and may be obtained in different crystal habits. Any reference herein, including the claims herein, to "compounds with which the invention is concerned" or "compounds of the invention" or "the present compounds", and the like, includes reference to the compounds irrespective of amorphous or polymorphic form.

Definitions

The following definitions shall apply throughout the specification and the appended claims, unless otherwise stated or indicated.

As used herein, the term "compound of the invention" refers to the 39 compounds listed above, and includes their pharmaceutically acceptable salts, hydrates, and solvate.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of the invention may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

In one aspect, the invention relates to a compound of the invention for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders, or inhibition of tumour growth.

In particular, it is believed that the compounds of the invention are useful for the treatment or prevention of arthritis (including rheumatoid arthritis, juvenile rheumatoid arthritis, osteoarthritis and psoriatic arthritis), synovitis, vasculitis, Sjogren's disease, a condition associated with inflammation of the bowel (including Crohn's disease, ulcerative colitis, inflammatory bowel disease and irritable bowel syndrome), atherosclerosis, multiple sclerosis, Alzheimer's disease, vascular dementia, Parkinson's disease, cerebral amyloid angiopathy, cerebral autosomal dominant arteriopathy with subcortical infarcts and leukoencephalopathy, a pulmonary inflammatory disease (including asthma, chronic obstructive pulmonary disease and acute respiratory distress syndrome), a fibrotic disease (including idiopathic pulmonary fibrosis, cardiac fibrosis, liver fibrosis and systemic sclerosis (scleroderma)), an inflammatory disease of the skin (including contact dermatitis, atopic dermatitis and psoriasis), an inflammatory disease of the eye (including age related macular degeneration, uveitis and diabetic retinopathy), systemic inflammatory response syndrome, sepsis, an inflammatory and/or autoimmune condition of the liver (including autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, an ischemic disease (including stroke and ischemia-reperfusion injury) or myocardial infarction and/or the complications thereof, or epilepsy.

In an embodiment, it is believed that the compounds of the invention are useful for the treatment or prevention of a disease selected from rheumatoid arthritis, osteoarthritis, liver fibrosis, chronic obstructive pulmonary disease, multiple sclerosis, Sjogren's disease, Alzheimer's disease, Parkinson's disease, inflammatory bowel disease, and vascular dementia.

In view of the evidence cited in the above introduction that VAP1 is up regulated in several cancers, including gastric cancer, melanoma, hepatoma and head and neck tumours and that mice bearing enzymatically inactive VAP-1 grow melanomas more slowly, and in view of the link between VAP1 and angiogenesis, it is also expected that the compounds of the invention are anti-angiogenic and therefore have utility in the treatment of cancers by inhibition of tumour growth.

The invention thus includes the compounds of the invention for use in the treatment or prevention of the above-mentioned conditions and diseases. The invention also includes the use of said compounds in the manufacture of a medicament for the treatment or prevention of the above-mentioned conditions and diseases. The invention furthermore includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

Compositions

A currently preferred embodiment of the invention is a pharmaceutical composition comprising a compound of the invention, together with one or more pharmaceutically acceptable carriers and/or excipients.

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg per kilo of body weight each. Normally, such a dosage is given orally but parenteral administration may also be chosen.

Preparation of Compounds of the Invention

The following abbreviations have been used:
Ac acetyl
AcOH acetic acid
Aq aqueous
Ar aryl
nBu n-butyl
Boc tertiary-butyloxycarbonyl
calcd calculated
conc concentrated
d day(s)
DCM dichloromethane
DIPEA diisopropylethylamine
DMA dimethylacetamide
DMF dimethylformamide
DMSO dimethyl sulfoxide
EDC N-(3-dimethylaminopropyl)-N'-ethylcarbodiimide
ES$^+$ electrospray ionization
Et$_3$N triethylamine
EtOAc ethyl acetate
EtOH ethanol
Ex Example
h hour(s)
HATU O-(7-azabenzotriazol-1-yl)-N,N,N.,N.-tetramethyluronium hexafluorophosphate
HBTU O-benzotriazole-N,N,N',N'-tetramethyl-uronium-hexafluoro phosphate
HPLC High Performance Liquid Chromatography
HRMS High Resolution Mass Spectrometry
Int Intermediate
LCMS Liquid Chromatography Mass Spectrometry
LDA Lithium diisopropylamide
M molar
MeCN acetonitrile
MeOH methanol
[MH]$^+$ protonated molecular ion
min minute(s)
MS Mass Spectrometry
NMP 1-methyl-2-pyrrolidinone
QTOF Quadrupole time-of-flight mass spectrometer
RP reverse phase
RT room temperature
Rt retention time
sat saturated
TFA trifluoroacetic acid
THF Tetrahydrofuran
UPLC Ultra Performance Liquid Chromatography
UV Ultra violet
XPhos 2-dicyclohexylphosphino-2',4',6'-triisopropylbiphenyl

EXAMPLES AND INTERMEDIATE COMPOUNDS

Experimental Methods

Reactions were conducted at room temperature unless otherwise specified. Microwave reactions were performed with a Biotage microwave reactor using process vials fitted with aluminium caps and septa. Hydrogenations were performed using a Thales H-Cube. Preparative low pressure chromatography was performed using a CombiFlash Companion or Combiflash RF systems equipped with RediSep or GraceResolv silica and C18 reverse phase columns. Preparative reverse phase HPLC was performed on a Gilson system with a UV detector equipped with a ACE-5AQ, 100×21.20 mm, 5 mm or Phenomenex Synergi Hydro-RP 80A AXIA, 100×21.20 mm, 4 mm columns. The purest fractions were collected, concentrated and dried under vacuum. Compounds were typically dried in a vacuum oven between 40° C. and 60° C. prior to purity analysis.

Compound analysis was performed by HPLC and LCMS. The HPLC data was collected using an Agilent 1100 HPLC system with diode array detector and the LCMS data was collected using an Agilent 1100 HPLC system with a Waters ZQ mass spectrometer connected. The standard chromatography method utilised a Phenomenex Synergi RP-Hydro column (150×4.6 mm, 4 μm), a gradient of 5-100% MeCN (+0.085% TFA) in water (+0.1% TFA) over 7 min at 1.5 mL per min and 30° C., with detection at 200-300 nm. Compound analysis was alternatively performed by UPLC using an Agilent UPLC 1290 Infinity system with a Kinetex XB RP column (100×2.1 mm, 1.7 μm), a gradient of 5-100% MeCN (+0.085% TFA) in water (+0.1% TFA) at 0.5 mL per min and 40° C., with detection at 200-300 nm or Kinetex XB RP column (50×2.1 mm, 1.7 μm), a gradient of 5-100% MeCN (+0.085% TFA) in water (+0.1% TFA) at 0.8 mL per min and 40° C., with detection at 200-300 nm.

The standard LCMS method for the intermediates utilised a Phenomenex Synergi RP-Hydro column (30×4.6 mm, 4 μm), a gradient of 5-100% MeCN (+0.085% TFA) in water (+0.1% TFA) over 1.75 min then 100% for 0.75 min at 1.5 mL per min and 30° C., with detection at 200-300 nm). The standard HPLC method for the Intermediates utilised a Zorbax XDB C18 column (50×4.6 mm, 1.8 μm), a gradient of 5-100% MeCN (+0.085% TFA) in water (+0.1% TFA) over 3.0 min then 100% for 0.5 min at 1.2 mL per min and 40° C., with detection at 200-300 nm.

Accurate masses were measured using a Waters QTOF electrospray ion source and corrected using Leucine Enkephalin lockmass. Spectra were acquired in positive and/or negative electrospray mode. The acquired mass range was m/z 100-1000. Test compounds were dissolved in DMSO to give a 10 mM stock solution. Typically 5 uL of the DMSO stock were diluted with 495 uL of acetonitrile and then further diluted with acetonitrile and water (1:1) to give a final concentration of 2 uM. The mass values reported correspond either to the parent molecule with a hydrogen added [MH] or with a hydrogen subtracted [M−H]. The compounds prepared were named using IUPAC.

Intermediate 1

5-Fluoro-N-(4-nitropyridin-3-yl)pyridin-2-amine

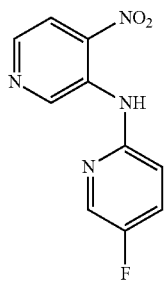

NaH (60% dispersion in mineral oil, 1.08 g, 27.1 mmol) was added portionwise to a solution of 2-amino-5-fluoropyridine (3.04 g, 27.1 mmol) in THF (60 mL) and the resultant mixture was stirred for 30 min. A solution of 3-fluoro-4-nitropyridine (3.50 g, 24.6 mmol) in THF (10 mL) was added and the resultant mixture was stirred for 16 h. The reaction mixture was partitioned between EtOAc (40 mL) and water (40 mL) and the organic phase was washed with brine (40 mL), dried (MgSO$_4$) and solvents were evaporated in vacuo. The residue was purified by column chromatography to give the title compound (1.76 g, 30.6%) as a red solid. LCMS (ES$^+$): 235.0 [M+H]$^+$. HPLC: Rt 5.51 min, 100% purity.

Intermediate 2

N-(5-Chloropyridin-2-yl)-4-nitropyridin-3-amine

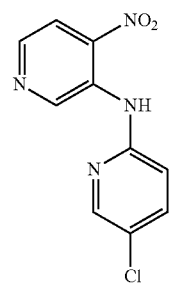

Intermediate 2 was prepared similarly to Intermediate 1, using 2-amino-5-chloropyridine instead of 2-amino-5-fluoropyridine, to give the title compound (1.24 g, 28.1%) as an orange solid. LCMS (ES$^+$): 251.0 [MH]$^+$. HPLC: Rt 5.92 min, 92.7% purity.

Intermediate 3

N-(5-Methylpyridin-2-yl)-4-nitropyridin-3-amine

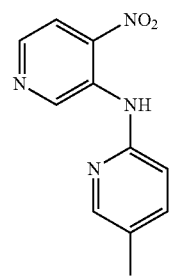

Intermediate 3 was prepared similarly to Intermediate 1, using 2-amino-5-methylpyridine instead of 2-amino-5-fluoropyridine, to give the title compound (1.25 g, 30.9%) as a red solid. LCMS (ES$^+$): 231.1 [MH]$^+$. HPLC: Rt 4.43 min, 80.3% purity.

Intermediate 4

3-[(2,4-Difluorophenyl)amino]-4-nitropyridin-1-ium-1-olate

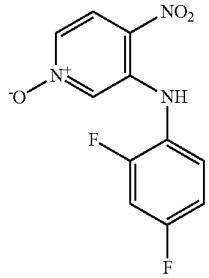

A mixture of 3-fluoro-4-nitropyridine N-oxide (2.00 g, 12.7 mmol) and 2,4-difluoroaniline (2.96 mL, 29.1 mmol) in EtOH (60 mL) was stirred at 70° C. for 16 h. The reaction mixture was cooled to RT and the precipitate isolated by vacuum filtration to give the title compound (2.16 g, 63.9%) as a yellow solid. LCMS (ES$^+$): 268.0 [M+H]$^+$. HPLC: Rt: 5.14 min, 99.3% purity.

Intermediates 5-7

Intermediates 5-7 were prepared similarly to Intermediate 4, by coupling of 3-fluoro-4-nitropyridine N-oxide with the appropriate aniline; see Table 1 below.

TABLE 1

SnAr formation of anilines

| Int | Structure | Name | Form, Yield, LCMS, HPLC |
|---|---|---|---|
| 5 | 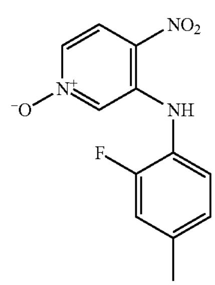 | 3-[(2-Fluoro-4-methylphenyl)amino]-4-nitropyridin-1-ium-1-olate | Orange solid<br>Yield 1.52 g, 91.5%<br>LCMS (ES$^+$): 264.0 [MH]$^+$<br>HPLC: Rt 5.63 min, 99.5% purity |
| 6 | 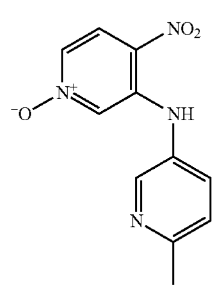 | 3-[(6-Methylpyridin-3-yl)amino]-4-nitropyridin-1-ium-1-olate | Orange solid<br>Yield 4.97 g, 79.7%<br>LCMS (ES$^+$): 247.0 [MH]$^+$<br>HPLC: Rt 2.92 min, 78.9% purity |
| 7 | 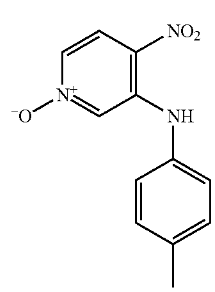 | 3-[(4-Methylphenyl)amino]-4-nitropyridin-1-ium-1-olate | Orange solid<br>Yield 4.99 g, 98.9%<br>LCMS (ES$^+$): 246.1 [MH]$^+$<br>HPLC: Rt 5.61 min, 100% purity |

Intermediate 8

3-[(4-Chlorophenyl)amino]-4-nitropyridin-1-ium-1-olate

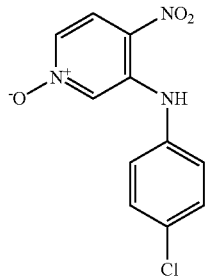

3-Bromo-4-nitropyridine N-oxide (10.0 g, 45.7 mmol) and 4-chloroaniline (17.5 g, 137 mmol) were dissolved in EtOH (100 mL) and heated to 60° C. for 18 h. The reaction mixture was cooled to RT and the precipitate was collected by filtration to give the title compound as an orange solid (2.83 g, 23.3%). LCMS (ES⁺): 266.0 [MH]⁺. HPLC: Rt 5.52 min, 100% purity.

Intermediate 9

3-[(4-Fluorophenyl)amino]-4-nitropyridin-1-ium-1-olate

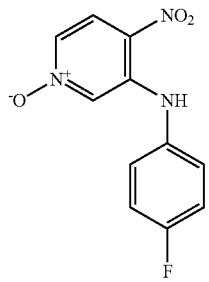

Intermediate 9 was prepared similarly to Intermediate 8, using 4-fluoroaniline instead of 4-chloroaniline, to give the title compound (10.4 g, 45.7%) as an orange solid. LCMS (ES⁺): 250.0 [MH]⁺. HPLC: Rt 5.15 min, 99.5% purity.

Intermediate 10

3-N-(2,4-Difluorophenyl)pyridine-3,4-diamine

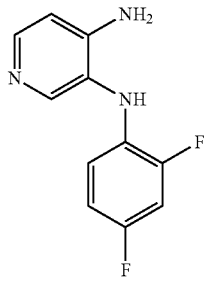 [SMILES: Nc1ccncc1Nc1ccc(F)cc1F]

Raney nickel (~50% slurry in water; 2.80 mL) was added slowly to a suspension of Intermediate 4 (2.16 g, 8.08 mmol) and hydrazine monohydrate (1.57 mL, 32.3 mmol) in EtOH (80 mL) and the resultant mixture was stirred for 90 min. The mixture was filtered through Celite and then washed with MeOH. The combined filtrate was evaporated in vacuo and then purified by column chromatography to give the title compound (1.32 g, 73.6%) as a pink solid. LCMS (ES⁺): 222.0 [M+H]⁺. HPLC: Rt: 4.08 min, 99.2% purity.

Intermediates 11-16

INTERMEDIATES 11-16 were prepared similarly to Intermediate 10, by reduction with Raney nickel of Intermediates 1 and 5-9 with either hydrazine hydrate or ammonium formate; see Table 2 below.

TABLE 2

Reduction of Intermediates 1 and 5-9 with Raney nickel and either hydrazine hydrate or ammonium formate.

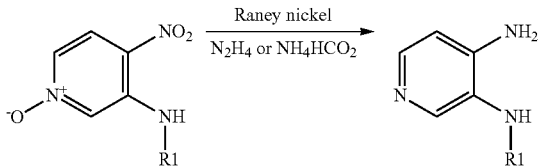

| Int | Structure | Name | Intermediate(s), Form, Yield, LCMS, HPLC |
|---|---|---|---|
| 11 | ![structure] | 3-N-(5-Fluoropyridin-2-yl)pyridine-3,4-diamine | From Intermediate 1<br>Purple oil<br>Yield 897 mg, 62.4%<br>LCMS(ES⁺): 205.1 [MH]⁺<br>HPLC: Rt 2.99 min, 99.6% purity |

TABLE 2-continued

Reduction of Intermediates 1 and 5-9 with Raney nickel and either hydrazine hydrate or ammonium formate.

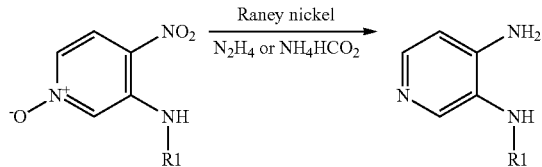

| Int | Structure | Name | Intermediate(s), Form, Yield, LCMS, HPLC |
|---|---|---|---|
| 12 | 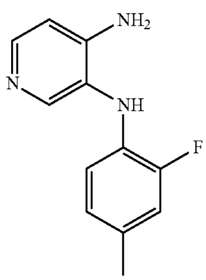 [SMILES: Cc1ccc(Nc2cnccc2N)c(F)c1] | 3-N-(2-Fluoro-4-methylphenyl)pyridine-3,4-diamine | From Intermediate 5<br>Purple solid<br>Yield 634 mg, 76.8%<br>LCMS (ES$^+$): 218.1 [MH]$^+$<br>HPLC: Rt 4.35 min, 90.5% purity |
| 13 | 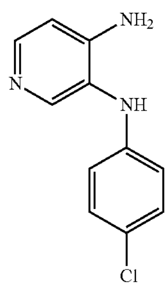 [SMILES: Nc1ccncc1Nc1ccc(Cl)cc1] | 3-N-(4-Chlorophenyl)pyridine-3,4-diamine | From Intermediate 8<br>Colourless gum<br>Yield 926 mg, 62.2%<br>LCMS (ES$^+$): 220.1 [MH]$^+$<br>HPLC: Rt 4.55 min, 97.8% purity |
| 14 | 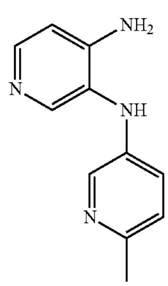 | 3-N-(6-Methylpyridin-3-yl)pyridine-3,4-diamine | From Intermediate 6<br>Orange gum<br>Yield 3.45 g, 85.2%<br>LCMS (ES$^+$): 201.1 [MH]$^+$ |
| 15 | 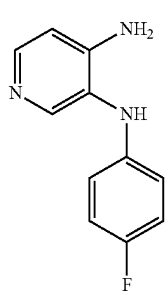 [SMILES: Nc1ccncc1Nc1ccc(F)cc1] | 3-N-(4-Fluorophenyl)pyridine-3,4-diamine | From Intermediate 9<br>Purple gum<br>Yield 7.18 g, 84.7%<br>LCMS (ES$^+$): 204.1 [MH]$^+$<br>HPLC: Rt 4.04 min, 100% purity |

TABLE 2-continued

Reduction of Intermediates 1 and 5-9 with Raney nickel and either hydrazine hydrate or ammonium formate.

| Int | Structure | Name | Intermediate(s), Form, Yield, LCMS, HPLC |
|---|---|---|---|
| 16 | 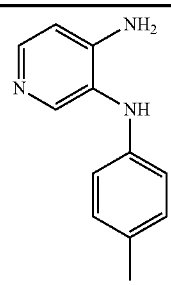 | 3-N-(4-Methylphenyl)pyridine-3,4-diamine | From Intermediate 7<br>Pale blue solid<br>Yield 5.01 g, 87.7%<br>LCMS (ES⁺): 200.1 [MH]⁺<br>HPLC: Rt 4.35 min, 100% purity |

Intermediate 17

3-N-(5-Chloropyridin-2-yl)pyridine-3,4-diamine

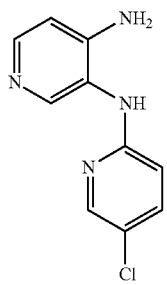

Intermediate 17 was prepared similarly to Intermediate 10, using Intermediate 2 instead of Intermediate 4, to give the title compound (804 mg, 74.3%) as a pink solid. LCMS (ES⁺): 221.1 [MH]⁺. UPLC: Rt 1.22 min, 100% purity.

Intermediate 18

N-(5-Methylpyridin-2-yl)-4-nitropyridin-3-amine

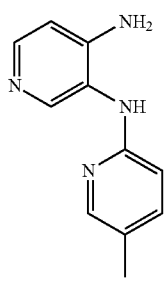

Intermediate 18 was prepared similarly to Intermediate 10, using Intermediate 3 instead of Intermediate 4, to give the title compound (885 mg, 81.4%) as a blue solid. LCMS (ES): 201.2 [MH]⁺. UPLC: Rt 0.29 min, 79.2% purity.

Intermediate 19

4-Methyl-6-(morpholin-4-yl)pyridine-3-carboxylic acid

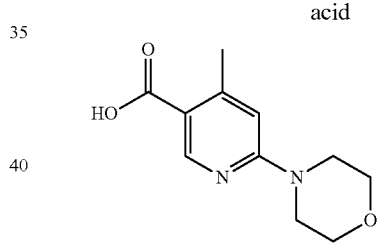

A solution of 6-fluoro-4-methylnicotinic acid (3.38 g, 21.8 mmol), morpholine (2.07 mL, 24.0 mmol) and Et₃N (3.80 mL, 27.2 mmol) in dioxane (30 mL) was heated at 110° C. for 20 h. The reaction mixture was cooled, the precipitate was removed by filtration and the filtrate evaporated to give the title compound (4.77 g, 98.4%) as a pale yellow solid. LCMS (ES⁺): 223.0 [M+H]⁺. HPLC: Rt 3.23 min, 96.0% purity.

Intermediate 20

2-[(Oxan-4-yl)amino]pyrimidine-5-carboxylic acid

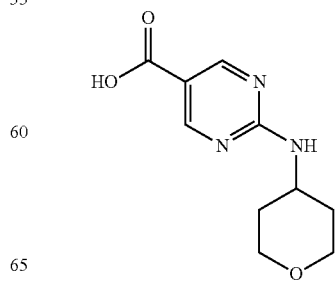

Intermediate 20 was prepared similarly to Intermediate 19, using 2-chloropyrimidine-5-carboxylic acid and 4-aminotetrahydropyran instead of 6-fluoro-4-methylnicotinic acid and morpholine respectively, to give the title compound (681 mg, 96.7%) as an off white solid. LCMS (ES+): 224.1 [MH]+. UPLC: Rt 1.57 min, 90.0% purity.

Intermediate 21

2-(Diethylamino)pyrimidine-5-carboxylic acid

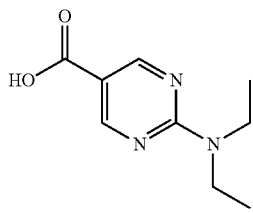

Intermediate 21 was prepared similarly to Intermediate 19, using 2-chloropyrimidine-5-carboxylic acid and diethylamine instead of 6-fluoro-4-methylnicotinic acid and morpholine respectively, to give the title compound (1.86 g, crude) as a pale orange oil. LCMS (ES+): 196.1 [MH]+. UPLC: Rt 2.12 min, 91.2% purity.

Intermediate 22

N-{3-[(5-Fluoropyridin-2-yl)amino]pyridin-4-yl}-6-(morpholin-4-yl)pyridine-3-carboxamide

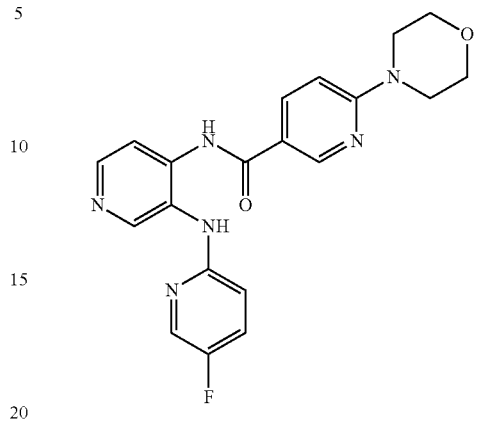

Et$_3$N (665 uL, 4.77 mmol) was added to a solution of 6-(morpholin-4-yl)nicotinic acid (365 mg, 1.75 mmol), HATU (787 mg, 2.07 mmol) in NMP (10 mL) and the resultant solution was stirred for 30 min. Intermediate 11 (325 mg, 1.59 mmol) was added and the resultant solution was stirred at 65° C. for 2 h. The reaction mixture was diluted with EtOAc (25 mL) and water (30 mL). The organic phase was washed with brine (20 mL), dried (MgSO$_4$) and solvents were evaporated in vacuo to yield a pink solid (628 mg, crude). LCMS (ES+): 395.0 [M+H]+.

Intermediates 23-30

Intermediates 23-30 were prepared similarly to Intermediate 22, by coupling of Intermediates 10, 12-16 and 18 with the appropriate carboxylic acid; see Table 3 below.

TABLE 3

Amide couplings

| Int | Structure | Name | Intermediate(s), Form, Yield, LCMS, HPLC |
|---|---|---|---|
| 23 | 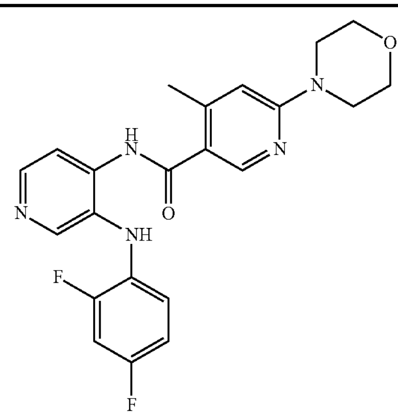 | N-{3-[(2,4-Difluorophenyl)amino]pyridin-4-yl}-4-methyl-6-(morpholin-4-yl)pyridine-3-carboxamide | From Intermediates 10 and 19<br>Orange solid<br>Yield 673 mg, crude<br>LCMS (ES+): 426.1 [MH]+ |

TABLE 3-continued

Amide couplings

| Int | Structure | Name | Intermediate(s), Form, Yield, LCMS, HPLC |
|---|---|---|---|
| 24 | 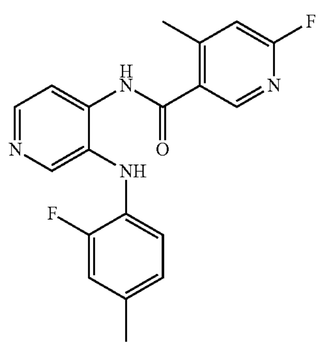 [SMILES: Cc1ccc(Nc2cnccc2NC(=O)c2cnc(F)cc2C)c(F)c1] | 6-Fluoro-N-{3-[(2-fluoro-4-methylphenyl)amino]pyridin-4-yl}-4-methylpyridine-3-carboxamide | From Intermediate 12<br>Yellow solid<br>Yield 212 mg, crude<br>LCMS (ES+): 355.0 [MH]+ |
| 25 | 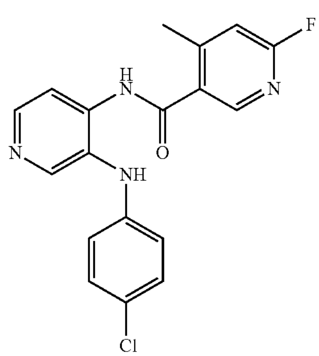 [SMILES: Cc1cc(F)ncc1C(=O)Nc1ccncc1Nc1ccc(Cl)cc1] | N-{3-[(4-Chlorophenyl)amino]pyridin-4-yl}-6-fluoro-4-methylpyridine-3-carboxamide | From Intermediate 13<br>Yellow solid<br>Yield 487 mg, crude<br>LCMS (ES+): 357.1 [MH]+ |
| 26 | 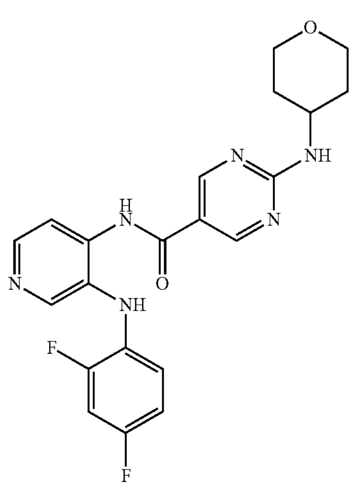 [SMILES: O=C(Nc1ccncc1Nc1ccc(F)cc1F)c1cnc(NC2CCOCC2)nc1] | N-{3-[(2,4-Difluorophenyl)amino]pyridin-4-yl}-2-[(oxan-4-yl)amino]pyrimidine-5-carboxamide | From Intermediates 10 and 20<br>Orange gum<br>Yield 482 mg, crude<br>LCMS (ES+): 427.1 [MH]+ |

TABLE 3-continued

Amide couplings

| Int | Structure | Name | Intermediate(s), Form, Yield, LCMS, HPLC |
|---|---|---|---|
| 27 | 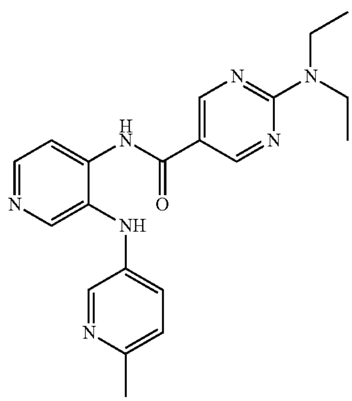 | 2-(Diethylamino)-N-{3-[(6-methylpyridin-3-yl)amino]pyridin-4-yl}pyrimidine-5-carboxamide | From Intermediates 14 and 21<br>Orange gum<br>Yield 471 mg, crude<br>LCMS (ES$^+$): 378.2 [MH]$^+$ |
| 28 | 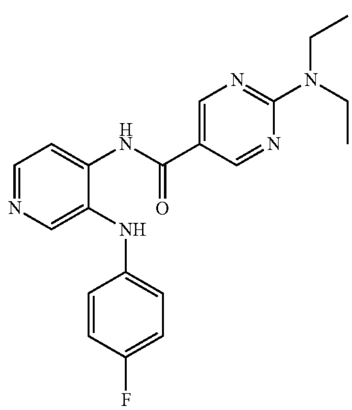 [SMILES: CCN(CC)c1ncc(C(=O)Nc2ccncc2Nc2ccc(F)cc2)cn1] | 2-(Diethylamino)-N-{3-[(4-fluorophenyl)amino]pyridin-4-yl}pyrimidine-5-carboxamide | From Intermediate 15 and 21<br>Orange gum<br>Yield 468 mg, crude<br>LCMS (ES$^+$): 381.1 [MH]$^+$ |
| 29 | 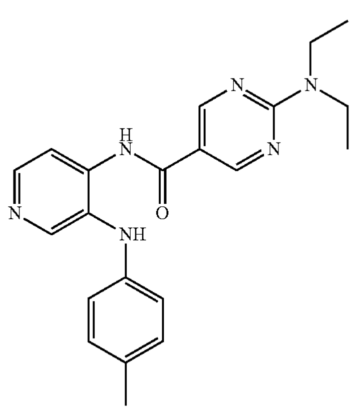 [SMILES: CCN(CC)c1ncc(C(=O)Nc2ccncc2Nc2ccc(C)cc2)cn1] | 2-(Diethylamino)-N-{3-[(4-methylphenyl)amino]pyridin-4-yl}pyrimidine-5-carboxamide | From Intermediate 16 and 21<br>Orange gum<br>Yield 472 mg, crude<br>LCMS (ES$^+$): 377.2 [MH]$^+$ |

TABLE 3-continued

Amide couplings

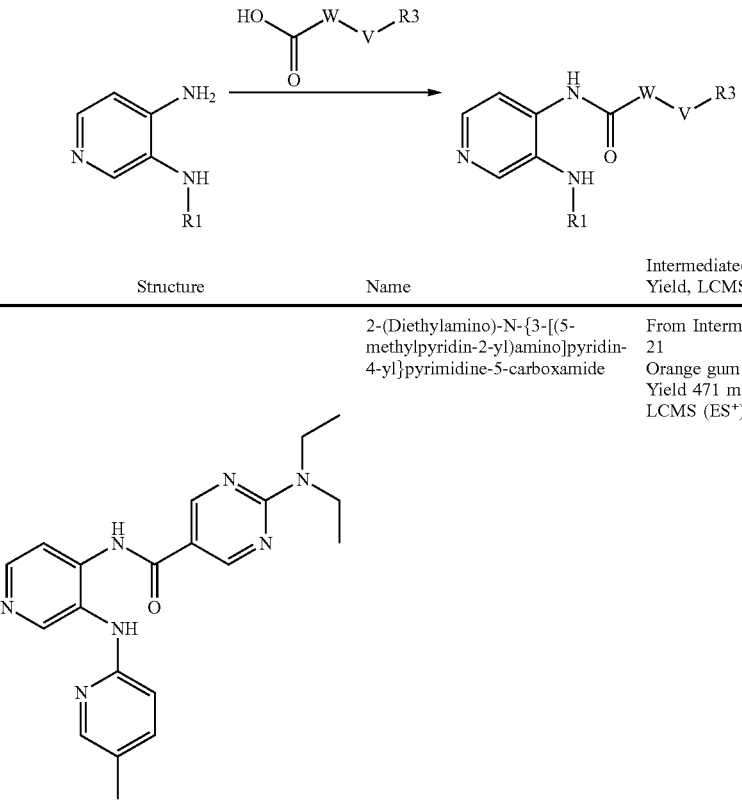

| Int | Structure | Name | Intermediate(s), Form, Yield, LCMS, HPLC |
|---|---|---|---|
| 30 | 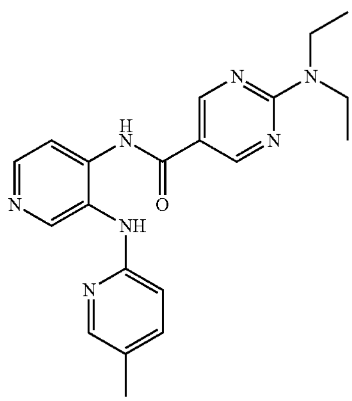 [SMILES: CCN(CC)c1ncc(C(=O)Nc2ccncc2Nc2ccc(C)cn2)cn1] | 2-(Diethylamino)-N-{3-[(5-methylpyridin-2-yl)amino]pyridin-4-yl}pyrimidine-5-carboxamide | From Intermediates 18 and 21<br>Orange gum<br>Yield 471 mg, crude<br>LCMS (ES+): 378.2 [MH]+ |

Intermediate 31

N-{3-[(5-Chloropyridin-2-yl)amino]pyridin-4-yl}-6-fluoro-4-methylpyridine-3-carboxamide

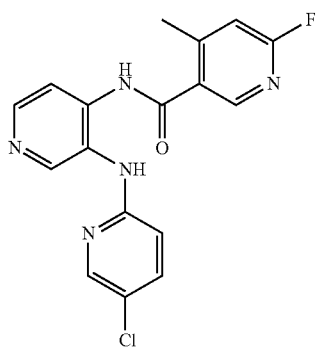 [SMILES: Cc1cc(F)ncc1C(=O)Nc1ccncc1Nc1ccc(Cl)cn1]

Oxalyl chloride (152 uL, 1.77 mmol) was added dropwise to a suspension of 2-fluoro-4-methylnicotinic acid (250 mg, 1.61 mmol) and DMF (12 uL, 161 umol) in DCM (6.0 mL) and the resultant solution was stirred for 30 min. A suspension of Intermediate 17 (320 mg, 1.45 mmol) and Et$_3$N (495 uL, 3.55 mmol) in DCM (5.0 mL) was added and the resultant mixture was stirred for 16 h. The reaction mixture was diluted with DCM (15 mL) and water (30 mL), the organic phase was washed with water (30 mL), brine (30 mL), dried (MgSO$_4$) and the solvents were evaporated in vacuo to give an orange oil (576 mg, crude). LCMS (ES+): 357.9 [M+H]+.

Intermediates 32-36

Intermediates 32-36 were prepared similarly to Intermediate 31, by carboxylic acid activation and coupling of Intermediates 11, 14-16 and 18; see Table 4 below.

TABLE 4

Carboxylic acid activation and subsequent coupling

| Int | Structure | Name | Intermediate(s), Form, Yield, LCMS, HPLC |
|---|---|---|---|
| 32 | 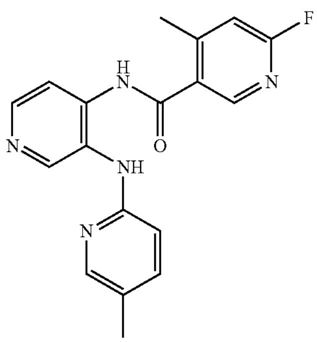 [SMILES: Cc1ccc(Nc2cnccc2NC(=O)c2cnc(F)cc2C)nc1] | 6-Fluoro-4-methyl-N-{3-[(5-methylpyridin-2-yl)amino]pyridin-4-yl}pyridine-3-carboxamide | From Intermediate 18<br>Brown gum<br>Yield 544 mg, crude<br>LCMS (ES+): 338.1 [MH]+ |
| 33 | 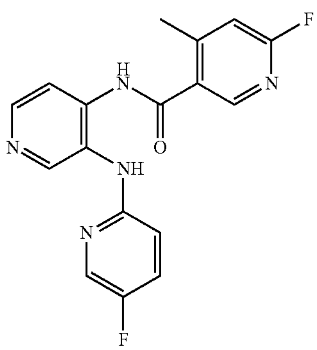 [SMILES: Cc1cc(F)ncc1C(=O)Nc1ccncc1Nc1ccc(F)cn1] | 6-Fluoro-N-{3-[(5-fluoropyridin-2-yl)amino]pyridin-4-yl}-4-methylpyridine-3-carboxamide | From Intermediate 11<br>Brown gum<br>Yield 396 mg, crude<br>LCMS (ES+): 342.1 [MH]+ |
| 34 | 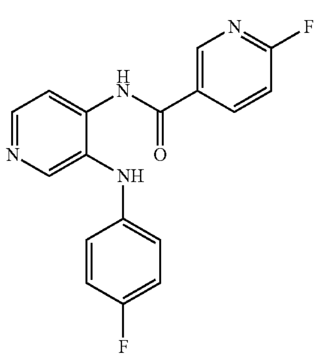 [SMILES: O=C(Nc1ccncc1Nc1ccc(F)cc1)c1ccc(F)nc1] | 6-Fluoro-N{3-[(4-fluorophenyl)amino]pyridin-4-yl}pyridine-3-carboxamide | From Intermediate 15<br>Off white solid<br>Yield 1.04 g, 65.1%<br>LCMS (ES+): 327.0 [MH]+<br>UPLC: Rt: 2.09 min, 96.9% purity |

TABLE 4-continued

Carboxylic acid activation and subsequent coupling

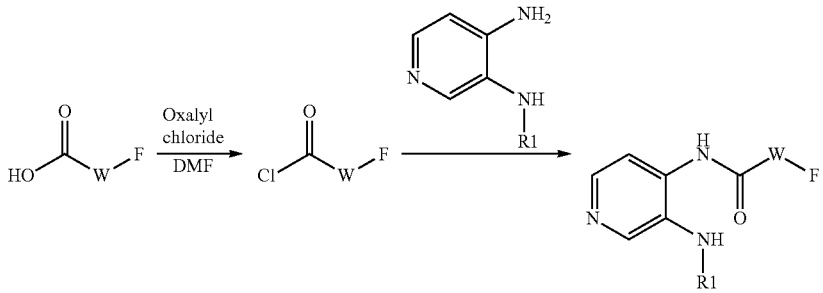

| Int | Structure | Name | Intermediate(s), Form, Yield, LCMS, HPLC |
|---|---|---|---|
| 35 | 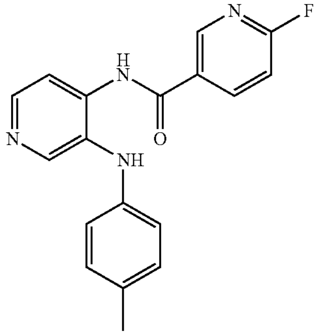 [SMILES: Cc1ccc(Nc2cnccc2NC(=O)c2ccc(F)nc2)cc1] | 6-Fluoro-N-{3-[(4-methylphenyl)amino]pyridin-4-yl}pyridine-3-carboxamide | From Intermediate 16<br>Pale green solid<br>Yield 567 mg, 53.9%<br>LCMS (ES+): 323.0 [MH]+<br>UPLC: Rt: 2.21 min, 95.6% purity |
| 36 | 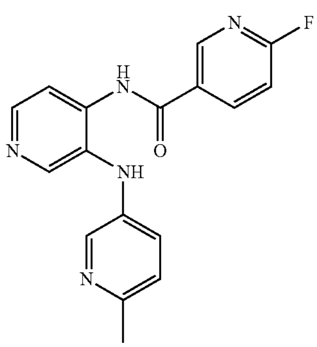 [SMILES: Cc1ccc(Nc2cnccc2NC(=O)c2ccc(F)nc2)cn1] | 6-Fluoro-N-{3-[(6-methylpyridin-3-yl)amino]pyridin-4-yl}pyridine-3-carboxamide | From Intermediate 14<br>Yellow solid<br>Yield 521 mg, 32.3%<br>LCMS (ES+): 324.0 [MH]+<br>UPLC: Rt: 1.09 min, 94.2% purity |

Intermediate 37

4-Bromo-N-{3-[(6-methylpyridin-3-yl)amino]pyridin-4-yl}benzamide

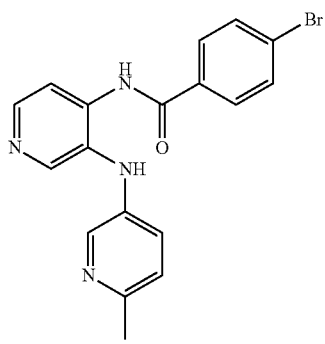 [SMILES: Cc1ccc(Nc2cnccc2NC(=O)c2ccc(Br)cc2)cn1]

4-Bromobenzoyl chloride (658 mg, 3.00 mmol) was added portionwise to a suspension of Intermediate 14 (600 mg, 3.00 mmol) in Et$_3$N (627 uL, 4.49 mmol) and DCM (12 mL) and the resultant solution was stirred for 1 h. The reaction was diluted with water (20 mL), the organic phase separated and the aqueous phase further extracted with DCM (20 mL). The combined organic phases were washed with brine (25 mL), dried (MgSO$_4$) and solvents were evaporated in vacuo to give the title compound (923 mg, 80.3%) as a yellow solid. LCMS (ES+): 383.0, 385.0 [M+H]+. UPLC: Rt 1.99 min, 95.6% purity.

Intermediates 38-40

Intermediates 38-40 were prepared similarly to Intermediate 37, by coupling of Intermediates 14 and 18 with the appropriate acid chloride; see Table 5 below.

TABLE 5

Acid chloride coupling

| Int | Structure | Name | Intermediate(s), Form, Yield, LCMS, HPLC |
|---|---|---|---|
| 38 | | 4-Bromo-2-fluoro-N-{3-[(6-methylpyridin-3-yl)amino]pyridin-4-yl}benzamide | From Intermediate 14<br>Maroon solid<br>Yield 1.20 g, crude<br>LCMS (ES+): 401.0 and 403.0 [MH]+ |
| 39 | | 4-Bromo-3-fluoro-N-{3-[(6-methylpyridin-3-yl)amino]pyridin-4-yl}benzamide | From Intermediate 14<br>Maroon solid<br>Yield 1.20 g, crude<br>LCMS (ES+): 401.0 and 403.0 [MH]+ |
| 40 | | 4-Bromo-N-{3-[(5-methylpyridin-2-yl)amino]pyridin-4-yl}benzamide | From Intermediate 18<br>Yellow solid<br>Yield 412 mg, 86.2%<br>LCMS (ES+): 382.9 384.9 [MH]+ |

Intermediate 41

5-[2-(4-Bromophenyl)-3H-imidazo[4,5-c]pyridin-3-yl]-2-methylpyridine

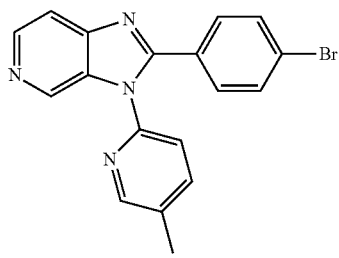 [SMILES: Cc1ccc(-n2c(-c3ccc(Br)cc3)nc3ccncc32)nc1]

Intermediate 37 (923 mg, 2.41 mmol) was dissolved in AcOH (4.5 mL) and the resultant solution was heated at 120° C. in a microwave reactor for 15 min. The reaction mixture was diluted with water (40 mL) and DCM (40 mL) and basified with solid $Na_2CO_3$ until~pH 9. The organic phase was washed with brine (40 mL), dried ($MgSO_4$) and solvents were evaporated in vacuo to give the title compound (664 mg, 75.5%) as an off-white solid. LCMS ($ES^+$): 364.9, 366.9 $[M+H]^+$. UPLC: Rt 2.16 min, 98.6% purity.

Intermediates 42-44

Intermediates 42-44 were prepared similarly to Intermediate 41, by acid mediated cyclisation of Intermediates 38-40; see Table 6 below.

TABLE 6

Cyclisation of Intermediates 38-40.

| Int | Structure | Name | Intermediate(s) used, Form, Yield, LCMS, HPLC |
|---|---|---|---|
| 42 | 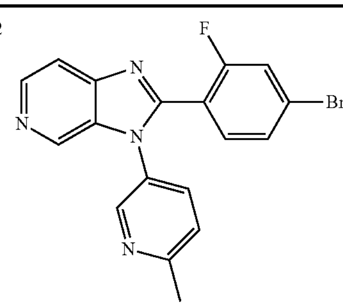 | 5-[2-(4-Bromo-2-fluorophenyl)-3H-imidazo[4,5-c]pyridin-3-yl]-2-methylpyridine | From Intermediate 38<br>Purple oil<br>Yield 17.0 mg, 2.64%<br>LCMS ($ES^+$): 383.0 and 385.0 $[MH]^+$.<br>UPLC: Rt 2.15 min, 96.3% purity. |
| 43 | 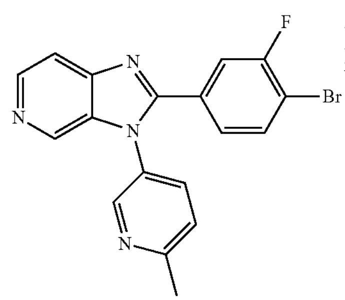 | 5-[2-(4-Bromo-3-fluorophenyl)-3H-imidazo[4,5-c]pyridin-3-yl]-2-methylpyridine | From Intermediate 39<br>Pale pink solid<br>Yield 515 mg, 44.9%<br>LCMS ($ES^+$): 383.0 and 385.0 $[MH]^+$.<br>UPLC: Rt 2.21 min, 92.2% purity |
| 44 | 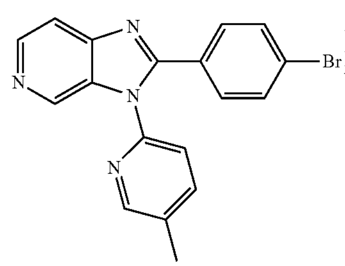 | 2-[2-(4-Bromophenyl)-3H-imidazo[4,5-c]pyridin-3-yl]-5-methylpyridine | From Intermediate 40<br>Off white solid<br>Yield 264 mg, 57.9%<br>LCMS ($ES^+$): 364.8 and 366.8 $[MH]^+$.<br>UPLC: Rt 2.34 min, 99.7% purity. |

Intermediate 45

6-Chloro-N-{3-[(4-chlorophenyl)amino]pyridin-4-yl}pyridine-3-carboxamide

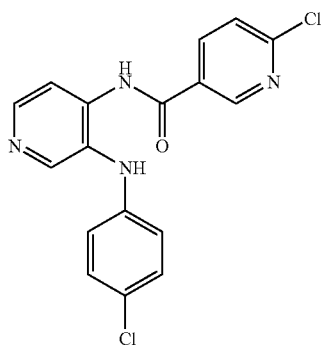 [SMILES: O=C(Nc1ccncc1Nc1ccc(Cl)cc1)c1ccc(Cl)nc1]

Intermediate 13 (302 mg, 1.38 mmol), 6-chloronicotinic acid (1.43 g, 4.54 mmol), HOBt (615 mg, 4.54 mmol) and DIPEA (1.87 mL, 10.7 mmol) were dissolved in DMF (6.0 mL) and treated with EDC (871 mg, 4.54 mmol). The reaction was stirred for 5.5 d. The mixture was poured into water (50 mL) and extracted with DCM (3×50 mL). The combined organic layers were dried (MgSO$_4$) and the solvents were removed in vacuo. The crude material was purified by column chromatography to give the title compound (163 mg, 32.9%) as a yellow gum. LCMS (ES$^+$): 359.0 [MH]$^+$.

Example 1

4-{5-[3-(5-Fluoropyridin-2-yl)-3H-imidazo[4,5-c]pyridin-2-yl]pyridin-2-yl}morpholine

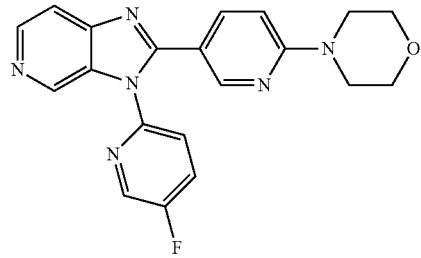 [SMILES: Fc1ccc(-n2c(-c3ccc(N4CCOCC4)nc3)nc3ccncc32)nc1]

Intermediate 22 (628 mg, 1.59 mmol) was suspended in AcOH (3.0 mL) and the resultant mixture was heated at 150° C. in a microwave reactor for 1 h. The reaction mixture was diluted with water (30 mL) and DCM (15 mL) and neutralised with Na$_2$CO$_3$ until the reaction mixture was pH ~8. The organic phase was isolated, washed with water (20 mL), brine (20 mL), dried (MgSO$_4$) and solvents were evaporated in vacuo to give a pink solid which was triturated in EtOH (2.5 mL) to give the title compound (25.0 mg, 4.17%) as a pink solid; HRMS (ES$^+$) calculated for [M+H] of C$_{20}$H$_{17}$FN$_6$O: 377.1526. found 377.1524. HPLC: Rt: 4.13 min, 98.4% purity.

Examples 2-7

Examples 2-7 were prepared similarly to Example 1, by acid mediated cyclisation of Intermediates 23 and 26-30; see Table 7 below.

TABLE 7

Cyclisation of Intermediates 23 and 26-30

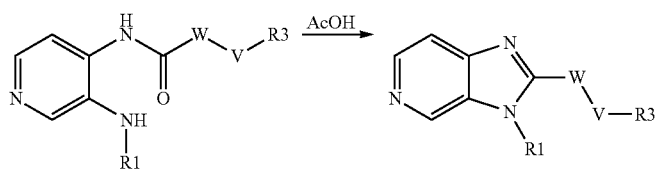

| Ex | Structure | Name | Intermediate(s) used, Form, Yield, LCMS, HPLC |
|---|---|---|---|
| 2 | 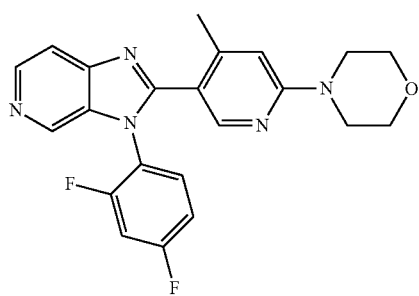 [SMILES: Cc1cc(N2CCOCC2)ncc1-c1nc2ccncc2n1-c1ccc(F)cc1F] | 4-{5-[3-(2,4-Difluorophenyl)-3H-imidazo[4,5-c]pyridin-2-yl]-4-methylpyridin-2-yl}morpholine | From Intermediate 23 Yellow solid Yield 17.0 mg, 2.64% HRMS (ES$^+$) calculated for [M + H] of C$_{22}$H$_{19}$F$_2$N$_5$O: 408.1636, found 408.1635. HPLC: Rt 4.25 min, 99.4% purity |

TABLE 7-continued

Cyclisation of Intermediates 23 and 26-30

| Ex | Structure | Name | Intermediate(s) used, Form, Yield, LCMS, HPLC |
|---|---|---|---|
| 3 | 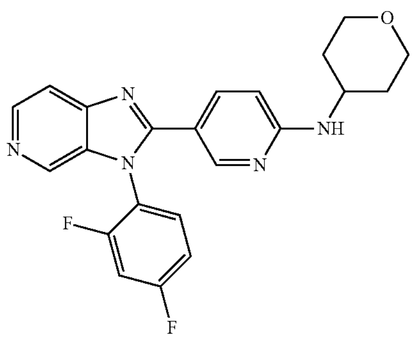 [SMILES: Fc1ccc(-n2c(-c3ccc(NC4CCOCC4)nc3)nc3ccncc32)c(F)c1] | 5-[3-(2,4-Difluorophenyl)-3H-imidazo[4,5-c]pyridin-2-yl]-N-(oxan-4-yl)pyrimidin-2-amine | From Intermediate 26<br>White solid<br>Yield 44.2 mg, 9.58%<br>HRMS (ES+) calculated for [M + H] of $C_{21}H_{16}F_2N_9O$: 409.1588, found 409.1587.<br>UPLC: Rt 1.99 min, 99.2% purity |
| 4 | 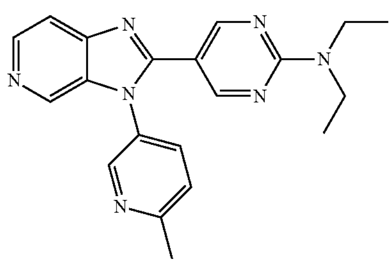 [SMILES: CCN(CC)c1ncc(-c2nc3ccncc3n2-c2ccc(C)nc2)cn1] | N,N-Diethyl-5-[3-(6-methylpyridin-3-yl)-3H-imidazo[4,5-c]pyridin-2-yl]pyrimidin-2-amine | From Intermediate 27<br>White solid<br>Yield 42.0 mg, 9.36%<br>HRMS (ES+) calculated for [M + H] of $C_{20}H_{21}N_7$: 360.1937, found 360.1935.<br>UPLC: Rt 2.12 min, 98.7% purity |
| 5 | 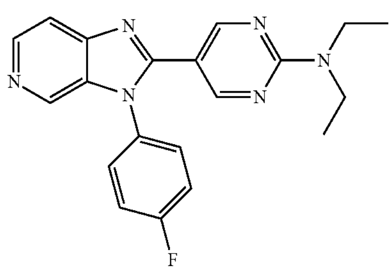 [SMILES: CCN(CC)c1ncc(-c2nc3ccncc3n2-c2ccc(F)cc2)cn1] | N,N-Diethyl-5-[3-(4-fluorophenyl)-3H-imidazo[4,5-c]pyridin-2-yl]pyrimidin-2-amine | From Intermediate 28<br>Orange solid<br>Yield 35.1 mg, 7.87%<br>HRMS (ES+) calculated for [M + H] of $C_{20}H_{19}FN_6$: 363.1733, found 363.1737.<br>UPLC: Rt2 .38 min, 98.7% purity |
| 6 | 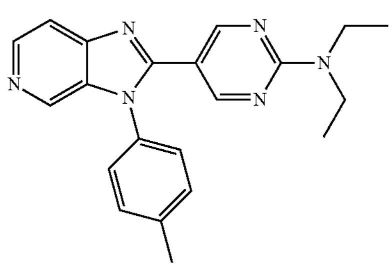 [SMILES: CCN(CC)c1ncc(-c2nc3ccncc3n2-c2ccc(C)cc2)cn1] | N,N-Diethyl-5-[3-(4-methylphenyl)-3H-imidazo[4,5-c]pyridin-2-yl]pyrimidin-2-amine | From Intermediate 29<br>Off white solid<br>Yield 27.0 mg, 6.00%<br>HRMS (ES+) calculated for [M + H] of $C_{21}H_{22}N_6$: 359.1984, found 359.1973.<br>UPLC: Rt 2.52 min, 99.3% purity |

TABLE 7-continued

Cyclisation of Intermediates 23 and 26-30

| Ex | Structure | Name | Intermediate(s) used, Form, Yield, LCMS, HPLC |
|---|---|---|---|
| 7 | 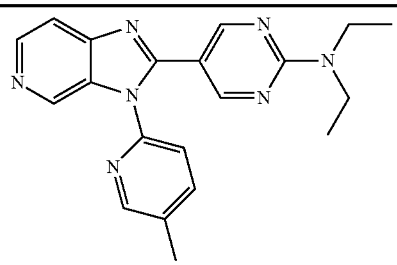 | N,N-Diethyl-5-[3-(5-methylpyridin-2-yl)-3H-imidazo[4,5-c]pyridin-2-yl]pyrimidin-2-amine | From Intermediate 30<br>White solid<br>Yield 34.2 mg, 7.62%<br>HRMS (ES$^+$) calculated for [M + H] of $C_{20}H_{21}N_7$: 360.1937, found 360.1938.<br>UPLC: Rt 2.31 min, 99.7% purity |

Example 8

4-{5-[3-(2-Fluoro-4-methylphenyl)-3H-imidazo[4,5-c]pyridin-2-yl]-4-methylpyridin-2-yl}morpholine

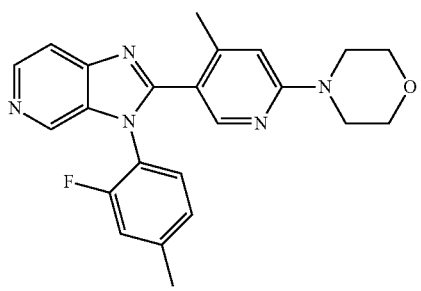 [SMILES: Cc1ccc(-n2c(-c3cnc(N4CCOCC4)cc3C)nc3ccncc32)c(F)c1]

Intermediate 24 (212 mg, 0.60 mmol) was dissolved in NMP (1.5 mL) and morpholine (310 uL, 3.59 mmol) was added. The resulting solution was heated at 180° C. in a microwave reactor for 30 min. The reaction mixture was cooled and partitioned between EtOAc (25 mL) and water (25 mL). The organic phase was washed with water (25 mL), brine (25 mL), dried (MgSO$_4$) and solvents were evaporated in vacuo. The residue was purified by reverse phase HPLC to give the title compound (22.0 mg, 9.1%) as a yellow solid. HRMS (ES$^+$) calculated for [M+H] of $C_{23}H_{22}FN_5O$: 404.1887. found 404.1888. HPLC: Rt 4.45 min, 99.3% purity.

Examples 9-11

Examples 9-11 were prepared similarly to Example 8, by SnAr and cyclisation of Intermediates 25 and 35 with the appropriate amine: see Table 8 below.

TABLE 8

SnAr and cyclisation of Intermediates 25 and 35.

| Ex | Structure | Name | Intermediate(s) used, Form, Yield, LCMS, HPLC |
|---|---|---|---|
| 9 | 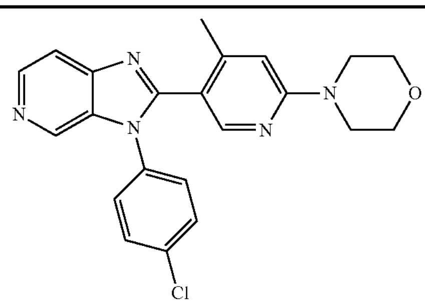 | 4-{5-[3-(4-Chlorophenyl)-3H-imidazo[4,5-c]pyridin-2-yl]-4-methylpyridin-2-yl}morpholine | From Intermediate 25<br>Off white solid<br>Yield 7.20 mg, 1.30%<br>HRMS (ES$^+$) calculated for [M + H] of $C_{22}H_{20}ClN_5O$: 406.1435, found 406.1433.<br>UPLC: Rt 1.99 min, 100% purity |

TABLE 8-continued

SnAr and cyclisation of Intermediates 25 and 35.

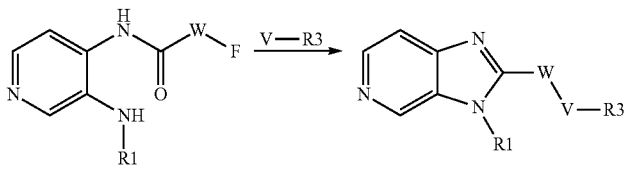

| Ex | Structure | Name | Intermediate(s) used, Form, Yield, LCMS, HPLC |
|---|---|---|---|
| 10 | 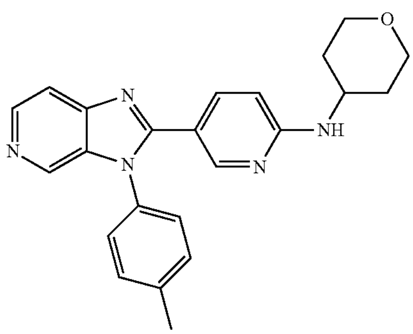 [SMILES: Cc1ccc(-n2c(-c3ccc(NC4CCOCC4)nc3)nc3ccncc32)cc1] | 5-[3-(4-Methylphenyl)-3H-imidazo[4,5-c]pyridin-2-yl]-N-(oxan-4-yl)pyridin-2-amine | From Intermediate 35<br>Off white solid<br>Yield 25.1 mg, 14.0%<br>HRMS (ES+) calculated for [M + H] of $C_{23}H_{23}N_5O$: 386.1981, found 386.1979.<br>UPLC: Rt 1.83 min, 98.8% purity |
| 11 | 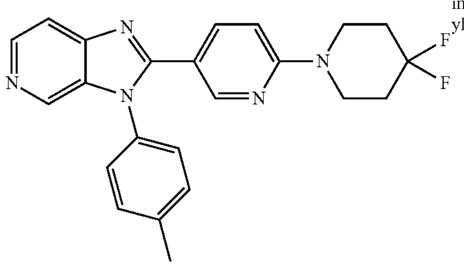 | 2-(4,4-Difluoropiperidin-1-yl)-5-[3-(4-methylphenyl)-3H-imidazo[4,5-c]pyridin-2-yl]pyridine | From Intermediate 35<br>White solid<br>Yield 47.0 mg, 24.9%<br>HRMS (ES+) calculated for [M + H] of $C_{23}H_{21}F_2N_5$: 406.1843, found 406.1842.<br>UPLC: Rt 2.44 min, 98.6% purity |

Examples 12

4-{5-[3-(5-Chloropyridin-2-yl)-3H-imidazo[4,5-c]pyridin-2-yl]-4-methylpyridin-2-yl}morpholine

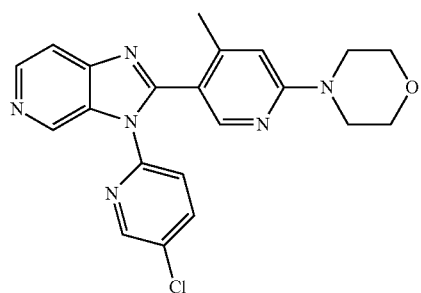

Intermediate 31 (576 mg, 1.61 mmol) and morpholine (695 uL, 8.06 mmol) were dissolved in NMP (1.5 mL) and the resultant solution was heated at 180° C. in a microwave reactor for 1 h. The reaction mixture was partitioned between EtOAc (20 mL) and water (20 mL) and the organic phase was washed with water (20 mL), brine (20 mL), dried (MgSO₄) and concentrated in vacuo. The residue was dissolved in AcOH (2.0 mL) and the resultant solution was heated at 150° C. in a microwave reactor for 30 min. The reaction mixture was diluted with water (10 mL) and DCM (10 mL) and basified by cautious addition of Na₂CO₃ until pH 9. The organic phase was washed with water (20 mL), brine (20 mL), dried (MgSO₄) and concentrated in vacuo. The residue was purified by reverse phase HPLC to give the title compound (80.0 mg, 12.2%) as an off-white solid. HRMS (ES+) calculated for [M+H] of $C_{21}H_{19}ClN_6O$: 407.1387. found 407.1385. UPLC: Rt: 1.90 min, 100% purity.

Examples 13-24

Examples 13-24 were prepared similarly to Example 12, by SnAr and cyclisation of Intermediates 32-36 with the appropriate amine and subsequent acid mediated cyclisation; see Table 9 below.

TABLE 9

SnAr and cyclisation of Intermediates 32-36

| Ex | Structure | Name | Intermediate(s), Form, Yield, LCMS, HPLC |
|---|---|---|---|
| 13 | 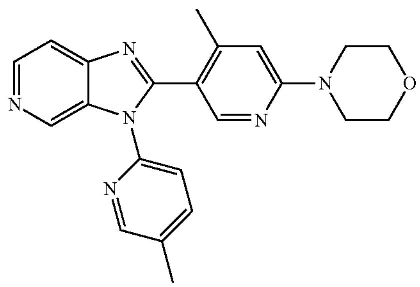 [SMILES: Cc1ccc(-n2c(-c3cnc(N4CCOCC4)cc3C)nc3ccncc32)nc1] | 4-{4-Methyl-5-[3-(5-methylpyridin-2-yl)-3H-imidazo[4,5-c]pyridin-2-yl]pyridin-2-yl}morpholine | From Intermediate 32<br>White solid<br>Yield 124 mg, 19.9%<br>HRMS (ES+) calculated for [M + H] of $C_{22}H_{22}N_6O$: 387.1933, found 387.1938.<br>UPLC: Rt: 1.82 min, 99.0% purity |
| 14 | 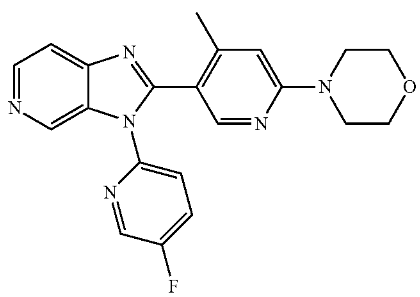 [SMILES: Cc1cc(N2CCOCC2)ncc1-c1nc2ccncc2n1-c1ccc(F)cn1] | 4-{5-[3-(5-Fluoropyridin-2-yl)-3H-imidazo[4,5-c]pyridin-2-yl]-4-methylpyridin-2-yl}morpholine; tris(trifluoroacetic acid) | From Intermediate 33<br>Yellow solid<br>Yield 18.0 mg, 2.12%<br>HRMS (ES+) calculated for [M + H] of $C_{21}H_{19}FN_6O$: 391.1682, found 391.1687.<br>UPLC: Rt: 1.78 min, 97.3% purity |
| 15 | 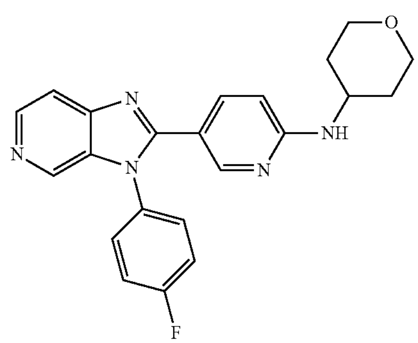 [SMILES: Fc1ccc(-n2c(-c3ccc(NC4CCOCC4)nc3)nc3ccncc32)cc1] | 5-[3-(4-Fluorophenyl)-3H-imidazo[4,5-c]pyridin-2-yl]-N-(oxan-4-yl)pyridin-2-amine | From Intermediate 34<br>Off white solid<br>Yield 40.0 mg, 22.3%<br>HRMS (ES+) calculated for [M + H] of $C_{22}H_{20}FN_5O$: 390.1730, found 390.1720.<br>UPLC: Rt: 1.74 min, 97.7% purity |
| 16 | 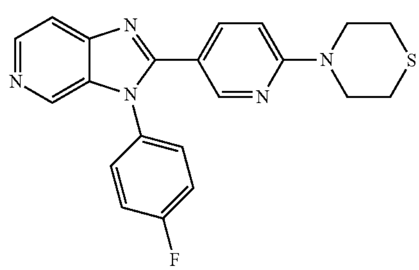 [SMILES: Fc1ccc(-n2c(-c3ccc(N4CCSCC4)nc3)nc3ccncc32)cc1] | 4-{5-[3-(4-Fluorophenyl)-3H-imidazo[4,5-c]pyridin-2-yl]pyridin-2-yl}thiomorpholine | From Intermediate 34<br>Off white solid<br>Yield 49.0 mg, 27.2%<br>HRMS (ES+) calculated for [M + H] of $C_{21}H_{16}FN_5S$: 392.1345, found 392.1335.<br>UPLC: Rt: 2.22 min, 99.2% purity |

TABLE 9-continued

SnAr and cyclisation of Intermediates 32-36

| Ex | Structure | Name | Intermediate(s), Form, Yield, LCMS, HPLC |
|---|---|---|---|
| 17 | 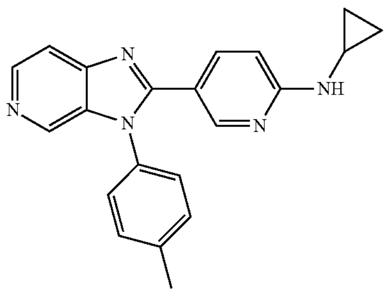 [SMILES: Cc1ccc(-n2c(-c3ccc(NC4CC4)nc3)nc3ccncc32)cc1] | N-Cyclopropyl-5-[3-(4-methylphenyl)-3H-imidazo[4,5-c]pyridin-2-yl]pyridin-2-amine | From Intermediate 35<br>Off white solid<br>Yield 24.1 mg, 15.2%<br>HRMS (ES+) calculated for [M + H] of $C_{21}H_{19}N_5$: 342.1718, found 342.1719.<br>UPLC: Rt: 1.60 min, 98.7% purity |
| 18 | 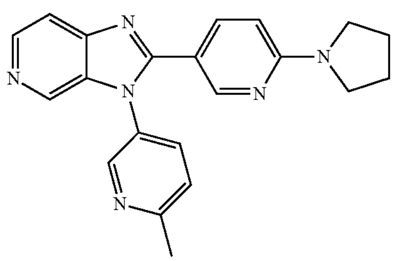 [SMILES: Cc1ccc(-n2c(-c3ccc(N4CCCC4)nc3)nc3ccncc32)cn1] | 5-[3-(6-Methylpyridin-3-yl)-3H-imidazo[4,5-c]pyridin-2-yl]-2-(pyrrolidin-1-yl)pyridine | From Intermediate 36<br>Off white solid<br>Yield 49.2 mg, 29.8%<br>HRMS (ES+) calculated for [M + H] of $C_{21}H_{20}N_9$: 357.1828, found 357.1826.<br>UPLC: Rt: 1.61 min, 99.7% purity |
| 19 | 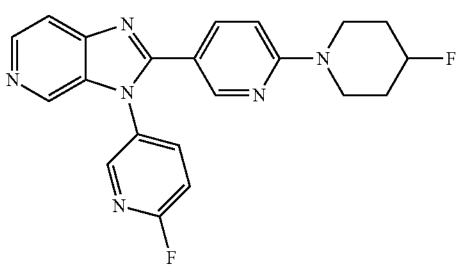 [SMILES: Fc1ccc(-n2c(-c3ccc(N4CCC(F)CC4)nc3)nc3ccncc32)cn1] | 2-(4-Fluoropiperidin-1-yl)-5-[3-(6-methylpyridin-3-yl)-3H-imidazo[4,5-c]pyridin-2-yl]pyridine | From Intermediate 36<br>Pale yellow solid<br>Yield 64.1 mg, 35.6%<br>HRMS (ES+) calculated for [M + H] of $C_{22}H_{21}FN_6$: 389.1890, found 389.1886.<br>UPLC: Rt: 1.91 min. 98.3% purity |
| 20 | 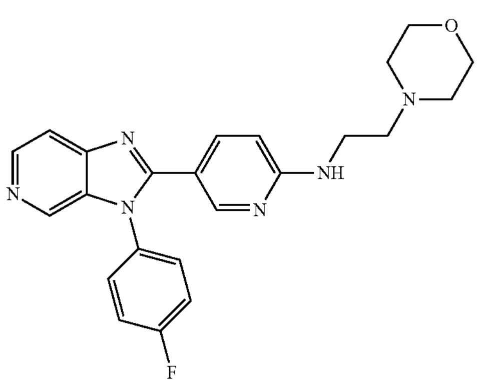 [SMILES: Fc1ccc(-n2c(-c3ccc(NCCN4CCOCC4)nc3)nc3ccncc32)cc1] | 5-[3-(4-Fluorophenyl)-3H-imidazo[4,5-c]pyridin-2-yl]-N-[2-(morpholin-4-yl)ethyl]pyridin-2-amine | From Intermediate 34<br>Off white solid<br>Yield 56.0 mg, 29.1%<br>HRMS (ES+) calculated for [M + H] of $C_{23}H_{23}FN_6O$: 419.1996, found 419.1984.<br>UPLC: Rt: 1.64 min, 98.6% purity |

TABLE 9-continued

SnAr and cyclisation of Intermediates 32-36

| Ex | Structure | Name | Intermediate(s), Form, Yield, LCMS, HPLC |
|---|---|---|---|
| 21 | 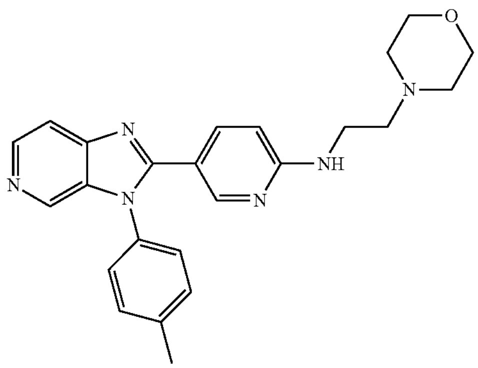 [SMILES: Cc1ccc(-n2c(-c3ccc(NCCN4CCOCC4)nc3)nc3ccncc32)cc1] | 5-[3-(4-Methylphenyl)-3H-imidazo[4,5-c]pyridin-2-yl]-N-[2-(morpholin-4-yl)ethyl]pyridin-2-amine | From Intermediate 35<br>Off white solid<br>Yield 35.1 mg, 18.2%<br>HRMS (ES$^+$) calculated for [M + H] of $C_{24}H_{26}N_6O$: 415.2246, found 415.2245.<br>UPLC: Rt: 1.73 min, 98.2% purity |
| 22 | 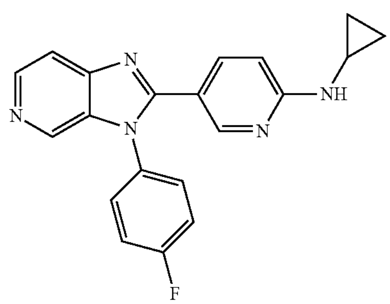 [SMILES: Fc1ccc(-n2c(-c3ccc(NC4CC4)nc3)nc3ccncc32)cc1] | N-Cyclopropyl-5-[3-(4-fluorophenyl)-3H-imidazo[4,5-c]pyridin-2-yl]pyridin-2-amine | From Intermediate 34<br>Pale yellow solid<br>Yield 75.5 mg, 35.6%<br>HRMS (ES$^+$) calculated for [M + H] of $C_{20}H_{16}FN_5$: 346.1468, found 346.1470.<br>UPLC: Rt: 1.75 min, 97.7% purity |
| 23 | 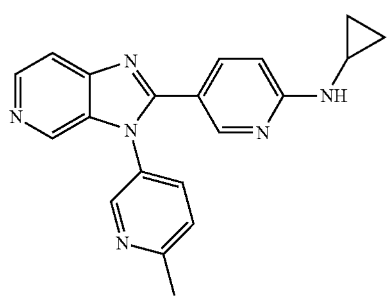 [SMILES: Cc1ccc(-n2c(-c3ccc(NC4CC4)nc3)nc3ccncc32)cn1] | N-Cyclopropyl-5-[3-(6-methylpyridin-3-yl)-3H-imidazo[4,5-c]pyridin-2-yl]pyridin-2-amine | From Intermediate 36<br>White solid<br>Yield 10.1 mg, 7.95%<br>HRMS (ES$^+$) calculated for [M + H] of $C_{20}H_{18}N_6$: 343.1671, found 343.1675.<br>UPLC: Rt: 1.54 min, 98.9% purity |
| 24 | 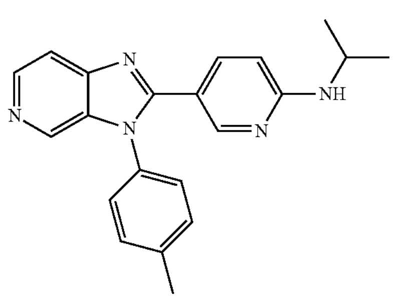 [SMILES: Cc1ccc(-n2c(-c3ccc(NC(C)C)nc3)nc3ccncc32)cc1] | 5-[3-(4-Methylphenyl)-3H-imidazo[4,5-c]pyridin-2-yl]-N-(propan-2-yl)pyridin-2-amine | From Intermediate 35<br>Pale yellow solid<br>Yield 28.0 mg, 13.1%<br>HRMS (ES$^+$) calculated for [M + H] of $C_{21}H_{21}N_5$: 344.1875, found 344.1876.<br>UPLC: Rt: 1.91 min, 100% purity |

Example 25

5-[3-(6-Methylpyridin-3-yl)-3H-imidazo[4,5-c]pyridin-2-yl]-2-(pyrrolidin-1-yl)pyrimidine

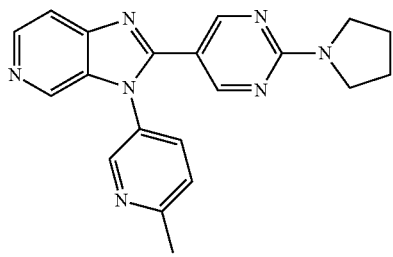

A suspension of Intermediate 14 (250 mg, 1.25 mmol), 2-pyrrolidin-1-ylpyrimidine-5-carbaldehyde (221 mg, 1.25 mmol) and $Na_2O_4S_2$ (652 mg, 3.75 mmol) in EtOH (3.0 mL) was heated at 150° C. in a microwave reactor for 90 min, with further $Na_2O_4S_2$ (652 mg, 3.75 mmol) added after 45 min. The reaction mixture was then poured into 1M aq $Na_2CO_3$ solution (25 mL) and extracted with DCM (2×25 mL). The combined organic phases were washed with brine (25 mL) dried ($MgSO_4$) and the solvents were evaporated in vacuo. The residue was triturated twice in MeOH (5.0 mL, then 4.0 mL) to give the title compound (127 mg, 28.5%) as a white solid. HRMS (ES$^+$) calculated for [M+H] of $C_{20}H_{19}N_7$: 358.1780, found 358.1779. UPLC: Rt 1.99 min, 99.2% purity.

Examples 26-30

Examples 26-30 were prepared similarly to Example 25, by reductive condensation of Intermediates 11, 14, 16 and 18 with the appropriate aldehyde; see Table 10 below.

TABLE 10

Reductive condensations of Intermediates 11, 14, 16 and 18.

| Ex | Structure | Name | Intermediate(s), Form, Yield, LCMS, HPLC |
|---|---|---|---|
| 26 | 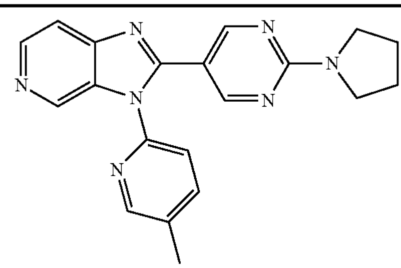 | 5-[3-(5-Methylpyridin-2-yl)-3H-imidazo[4,5-c]pyridin-2-yl]-2-(pyrrolidin-1-yl)pyrimidine | From Intermediate 18<br>White solid<br>Yield 48.2 mg, 13.5%<br>HRMS (ES$^+$) calculated for [M + H] of $C_{20}H_{19}N_7$: 358.1780, found 358.1772.<br>UPLC: Rt: 2.12 min, 99.2% purity |
| 27 | 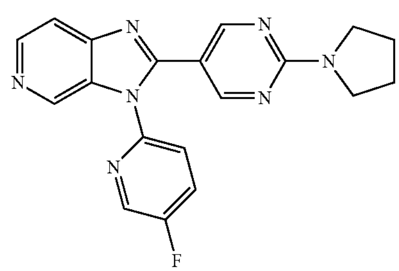 [SMILES: Fc1ccc(-n2c(-c3cnc(N4CCCC4)nc3)nc3ccncc32)nc1] | 5-[3-(5-Fluoropyridin-2-yl)-3H-imidazo[4,5-c]pyridin-2-yl]-2-(pyrrolidin-1-yl)pyrimidine | From Intermediate 11<br>White solid<br>Yield 17.1 mg, 4.83%<br>HRMS (ES$^+$) calculated for [M + H] of $C_{19}H_{16}FN_7$: 362.1529, found 362.1530.<br>UPLC: Rt: 2.12 min, 98.8% purity |
| 28 | 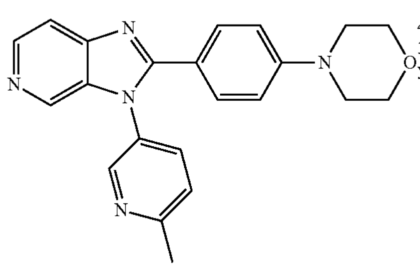 [SMILES: Cc1ccc(-n2c(-c3ccc(N4CCOCC4)cc3)nc3ccncc32)cn1] | 4-{4-[3-(6-Methylpyridin-3-yl)-3H-imidazo[4,5-c]pyridin-2-yl]phenyl}morpholine | From Intermediate 14<br>White solid<br>Yield 32.1 mg, 8.65%<br>HRMS (ES$^+$) calculated for [M + H] of $C_{22}H_{21}N_5O$: 372.1824, found 372.1812.<br>UPLC: Rt: 1.95 min, 99.1% purity |

TABLE 10-continued

Reductive condensations of Intermediates 11, 14, 16 and 18.

| Ex | Structure | Name | Intermediate(s), Form, Yield, LCMS, HPLC |
|---|---|---|---|
| 29 | 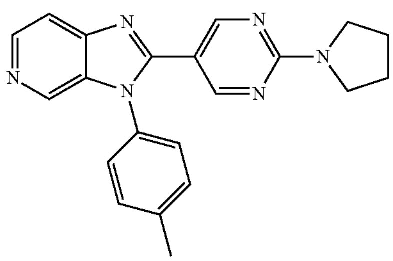 | 5-[3-(4-Methylphenyl)-3H-imidazo[4,5-c]pyridin-2-yl]-2-(pyrrolidin-1-yl)pyrimidine | From Intermediate 16<br>White solid<br>Yield 96.5 mg, 27.0%<br>HRMS (ES$^+$) calculated for [M + H of $C_{21}H_{20}N_6$: 357.1828, found 357.1828,<br>UPLC: Rt: 2.32 min, 99.4% purity |
| 30 | 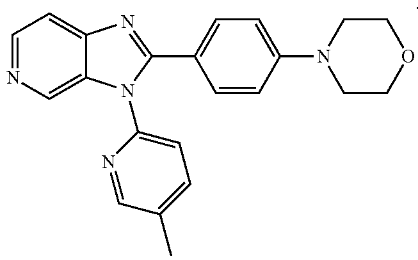 | 4-{4-[3-(5-Methylpyridin-2-yl)-3H-imidazo[4,5-c]pyridin-2-yl]phenyl}morpholine | From Intermediate 18<br>White solid<br>Yield 36.0 mg, 12.9%<br>HRMS (ES$^+$) calculated for [M + H] of $C_{22}H_{21}N_5O$: 372.1824, found 372.1818.<br>UPLC: Rt: 2.13 min, 100% purity |

Example 31

2-Methyl-5-{2-[4-(pyrrolidin-1-yl)phenyl]-3H-imidazo[4,5-c]pyridin-3-yl}pyridine

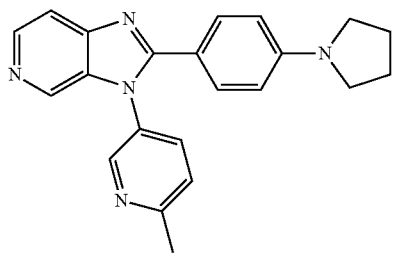

A mixture of Intermediate 41 (200 mg, 548 umol), pyrrolidine (49.5 uL, 602 umol), XPhos (52.2 mg, 110 umol), Pd$_2$(dba)$_3$ (50.1 mg, 54.8 umol) and NaOtBu (63.2 mg, 657 umol) in dioxane (2.0 mL) was heated at 100° C. for 16 h. The reaction mixture was partitioned between DCM (20 mL) and water (20 mL) and the organic phase was washed with brine (20 mL), dried (MgSO$_4$) and concentrated in vacuo. The resulting residue was triturated in MeOH (3.0 mL) to give the title compound (18.1 mg, 9.30%) as a beige solid. HRMS (ES$^+$) calculated for [M+H] of $C_{22}H_{21}N_5$: 356.1875. found 356.1877. UPLC: Rt 2.30 min, 98.7% purity.

Examples 32-37

Examples 32-37 were prepared similarly to Example 31, by Buchwald Hartwig coupling of Intermediates 41-44, with the appropriate amine; see Table 11 below.

TABLE 11

Buchwald Hartwig coupling of Intermediates 41-44,

X = Cl or Br

Pd(OAc)₂, XPhos, t-BuONa, dioxane, 120° C., V—R3

| Ex | Structure | Name | Intermediate(s), Form, Yield, LCMS, HPLC |
|---|---|---|---|
| 32 | 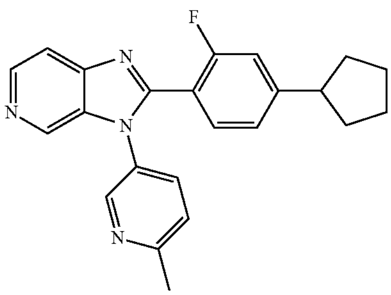 [SMILES: Cc1ccc(-n2c(-c3ccc(C4CCCC4)cc3F)nc3ccncc32)cn1] | 5-{2-[2-Fluoro-4-(pyrrolidin-1-yl)phenyl]-3H-imidazo[4,5-c]pyridin-3-yl}-2-methylpyridine | From Intermediate 42<br>Yellow gum<br>Yield 7.10 mg, 4.86%<br>HRMS (ES⁺) calculated for [M + H] of $C_{22}H_{20}FN_5$: 374.1781, found 374.1790.<br>UPLC: Rt: 2.30 min, 98.1% purity |
| 33 | 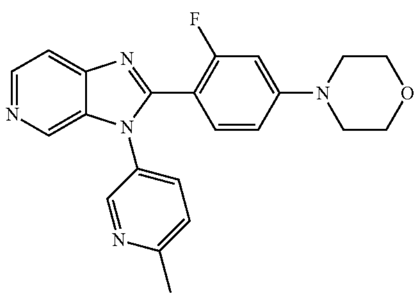 [SMILES: Cc1ccc(-n2c(-c3ccc(N4CCOCC4)cc3F)nc3ccncc32)cn1] | 4-{3-Fluoro-4-[3-(6-methylpyridin-3-yl)-3H-imidazo[4,5-c]pyridin-2-yl]phenyl}morpholine | From Intermediate 42<br>White solid<br>Yield 48.4 mg, 31.8%<br>HRMS (ES⁺) calculated for [M + H] of $C_{22}H_{20}FN_5O$: 390.1730. found 390.1725.<br>UPLC: Rt: 1.98min, 99.1% purity |
| 34 | 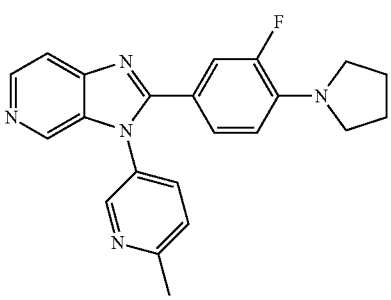 [SMILES: Cc1ccc(-n2c(-c3ccc(N4CCCC4)c(F)c3)nc3ccncc32)cn1] | 5-{2-[3-Fluoro-4-(pyrrolidin-1-yl)phenyl]-3H-imidazo[4,5-c]pyridin-3-yl}-2-methylpyridine | From Intermediate 43<br>Yellow solid<br>Yield 11.0 mg, 5.64%<br>HRMS (ES⁺) calculated for [M + H] of $C_{22}H_{20}FN_5$: 374.1781, found 374.1782.<br>UPLC: Rt: 2.38 min, 99.1% purity |
| 35 | 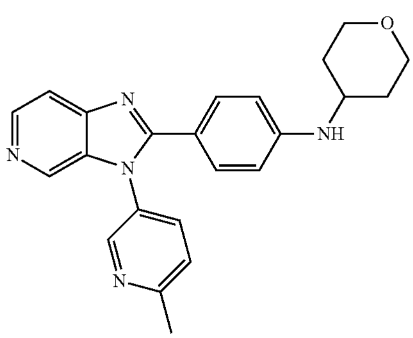 [SMILES: Cc1ccc(-n2c(-c3ccc(NC4CCOCC4)cc3)nc3ccncc32)cn1] | N-{4-[3-(6-Methylpyridin-3-yl)-3H-imidazo[4,5-c]pyridin-2-yl]phenyl}oxan-4-amine | From Intermediate 41<br>White solid<br>Yield 55.2 mg, 26.2%<br>HRMS (ES⁺) calculated for [M + H] of $C_{23}H_{23}N_5O$: 386.1981, found 386.1987.<br>UPLC: Rt: 1.97min, 99.0% purity |

TABLE 11-continued

Buchwald Hartwig coupling of Intermediates 41-44.

Pd(OAc)₂, XPhos
t-BuONa, dioxane, 120° C.
V—R3

X = Cl or Br

| Ex | Structure | Name | Intermediate(s), Form, Yield, LCMS, HPLC |
|---|---|---|---|
| 36 | 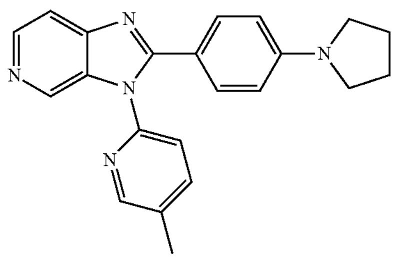 | 5-Methyl-2-{2-[4-(pyrrolidin-1-yl)phenyl]-3H-imidazo[4,5-c]pyridin-3-yl}pyridine | From Intermediate 44<br>Off white solid<br>Yield 50.2 mg, 41.3%<br>HRMS (ES⁺) calculated for [M + H] of $C_{22}H_{21}N_5$: 356.1875, found 356.1879.<br>UPLC: Rt: 2.48 min, 98.7% purity |
| 37 | 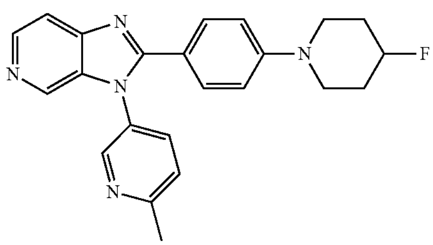 [SMILES: Cc1ccc(-n2c(-c3ccc(N4CCC(F)CC4)cc3)nc3ccncc32)cn1] | 5-{2-[4-(4-Fluoropiperidin-1-yl)phenyl]-3H-imidazo[4,5-c]pyridin-3-yl}-2-methylpyridine | From Intermediate 41<br>White solid<br>Yield 21.0 mg, 15.8%<br>HRMS (ES⁺) calculated for [M + H] of $C_{23}H_{22}FN_5$: 388.1937, found 388.1941.<br>UPLC: Rt: 2.19 min, 100% purity |

Example 38

2-Chloro-5-[3-(4-chlorophenyl)-3H-imidazo[4,5-c]pyridin-2-yl]pyridine

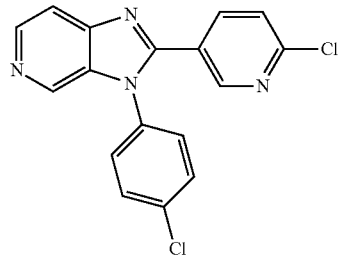 [SMILES: Clc1ccc(-n2c(-c3ccc(Cl)nc3)nc3ccncc32)cc1]

Intermediate 45 (163 mg, 0.45 mmol) was dissolved in AcOH (5 mL) and heated at 100° C. in a microwave reactor for 15 min. The reaction mixture was poured into water (50 mL), basified with Na₂CO₃ and extracted with DCM (3×50 mL). The combined organic layers were dried (MgSO₄) and the solvents were removed in vacuo. The residue was purified by reverse phase HPLC to yield the title compound (55.6 mg, 36.0%) as a white solid. HRMS (ES⁺) calculated for [M+H] of $C_{17}H_{10}Cl_2N_4$: 341.0361. found 341.0352. HPLC: Rt 5.13 min, 99.9% purity.

Example 39

2-Chloro-5-[3-(4-fluorophenyl)-3H-imidazo[4,5-c]pyridin-2-yl]pyridine

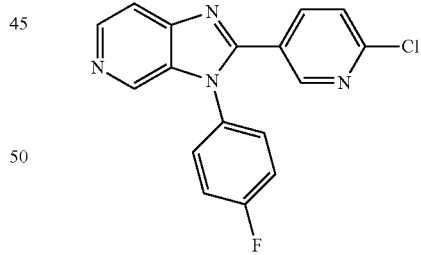

A suspension of Intermediate 9 (800 mg, 3.21 mmol), 2-chloropyridine-5-carboxaldehyde (568 mg, 4.01 mmol) and Na₂S₂O₄ (2.24 g, 12.8 mmol) in EtOH (10 mL) was heated using in a microwave reactor at 160° C. for 1 h. The reaction mixture was then poured into 1M Na₂CO₃ solution (50 mL) and extracted with DCM (3×50 mL). The combined organic phases were dried (MgSO₄) and the solvents were evaporated in vacuo. The residue was purified by column chromatography to give the title compound as an off white solid (39.0 mg, 7.48%). HRMS (ES⁺) calculated for [M+H] of $C_{17}H_{10}ClFN_4$: 325.0656, found 325.0642. HPLC: Rt: 4.76 min, 99.5%.

Biological Tests
Biological Assays of the SSAO Enzyme Inhibitors

All primary assays were performed at RT. with purified recombinantly expressed human SSAO. Enzyme was prepared essentially as described in Öhman et al. (Protein Expression and Purification 46 (2006) 321-331). In addition, secondary- and selectivity assays were performed using SSAO prepared from various tissues or purified rat recombinant SSAO. The enzyme activity was assayed with benzylamine as substrate by measuring either benzaldehyde production, using $^{14}C$-labeled substrate, or by utilizing the production of hydrogen peroxide in a horseradish peroxidase (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and compounds in 50 mM sodium phosphate, pH 7.4 were set to pre-incubate in flat-bottomed microtiter plates for approximately 15 min before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 h, exciting at 544 nm and reading the emission at 590 nm. For the human SSAO assay final concentrations of the reagents in the assay wells were: SSAO enzyme 1 ug/mL, benzylamine 100 uM, Amplex reagent 20 uM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and $IC_{50}$ values were calculated using the GraphPad Prism 4 or XLfit 4 programs.

Aldehyde Detection:

SSAO activity was assayed using 140-labeled benzylamine and analysed by measuring radioactive benzaldehyde. In a white 96-well optiplate (Packard), 20 uL of diluted test compound was pre-incubated at RT with 20 uL SSAO enzyme for approximately 15 min with continuous agitation. All dilutions were made with PBS. The reaction was initiated by adding 20 uL of the benzylamine substrate solution containing [7-140] Benzylamine hydrochloride (CFA589, GE Healthcare). The plate was incubated for 1 h as above after which the reaction was stopped by acidification (10 uL 1M aq HCl). Then 90 uL Micro Scint-E solution (Perkin-Elmer) was added to each well and the plate was continuously mixed for 15 min. Phase separation occurred instantly and activity was read in a Topcount scintillation counter (Perkin-Elmer). In the final reaction well, the human recombinant SSAO concentration was 10 ug/mL. In order to optimize sensitivity, the substrate concentration was decreased as compared to the HRP coupled assay in order to get a higher fraction of radioactive product. In the human SSAO assay, benzylamine concentration was 40 uM (0.2uCi/mL). Data was analysed as above.

All of the exemplified compounds of the invention had an $IC_{50}$ value of between 1 nM and 1200 nM at SSAO (see Table 12 below).

TABLE 12

SSAO inhibitory activity (A: <50 nM, B: 50-200 nM, C: 200-1200 nM)

| Compound | SSAO $IC_{50}$ (nM) |
|---|---|
| 1 | B |
| 2 | A |
| 3 | B |
| 4 | B |
| 5 | A |
| 6 | A |
| 7 | B |
| 8 | A |
| 9 | A |
| 10 | A |
| 11 | A |
| 12 | A |
| 13 | B |
| 14 | C |
| 15 | A |
| 16 | A |
| 17 | A |
| 18 | A |
| 19 | A |
| 20 | A |
| 21 | A |
| 22 | A |
| 23 | C |
| 24 | A |
| 25 | B |
| 26 | B |
| 27 | B |
| 28 | B |
| 29 | A |
| 30 | C |
| 31 | A |
| 32 | A |
| 33 | B |
| 34 | B |
| 35 | C |
| 36 | B |
| 37 | B |
| 38 | C |
| 39 | C | hERG Assay

Compounds of the invention were tested for inhibition of the human ether a go-go related gene (hERG) $K^+$ channel using IonWorks patch clamp electrophysiology. 8 Point concentration-response curves were generated on two occasions using 3-fold serial dilutions from the maximum assay concentration (11 uM). Electrophysiological recordings were made from a Chinese Hamster Lung cell line stably expressing the full length hERG channel. Single cell ion currents were measured in the perforated patch clamp configuration (100 ug/mL amphoterocin) at RT using an IonWorks Quattro instrument. The internal solution contained 140 mM KCl, 1 mM $MgCl_2$, 1 mM EGTA and 20 mM HEPES and was buffered to pH 7.3. The external solution contained 138 mM NaCl, 2.7 mM KCl, 0.9 mM $CaCl_2$, 0.5 mM $MgCl_2$, 8 mM $Na_2HPO_4$ and 1.5 mM $KH_2PO_4$, and was buffered to pH 7.3. Cells were clamped at a holding potential of 70 mV for 30 s and then stepped to +40 mV for 1 s. This was followed by a hyperpolarising step of 1 s to 30 mV to evoke the hERG tail current. This sequence was repeated 5 times at a frequency of 0.25 Hz. Currents were measured from the tail step at the $5^{th}$ pulse, and referenced to the holding current. Compounds were incubated for 6-7 min prior to a second measurement of the hERG signal using an identical pulse train. A minimum of 17 cells were required for each pIC50 curve fit. A control compound (quinidine) was used (see Table 13 below).

TABLE 13

| hERG IC50 (A: >10uM, B: 1-10 uM, C: 0.1M-1 uM) | |
|---|---|
| Compound | hERG IC50 |
| 10 | A |
| 12 | A |
| 15 | A |
| 17 | A |
| 18 | A |
| 19 | A |
| 21 | A |

The invention claimed is:
1. A compound selected from the group consisting of:
4-{5-[3-(5-Fluoropyridin-2-yl)-3H-imidazo[4,5-c]pyridin-2-yl]pyridin-2-yl}morpholine;
4-{5-[3-(2,4-Difluorophenyl)-3H-imidazo[4,5-c]pyridin-2-yl]-4-methylpyridin-2-yl}morpholine;
5-[3-(2,4-Difluorophenyl)-3H-imidazo[4,5-c]pyridin-2-yl]-N-(oxan-4-yl)pyrimidin-2-amine;
N,N-Diethyl-5-[3-(6-methylpyridin-3-yl)-3H-imidazo[4,5-c]pyridin-2-yl]pyrimidin-2-amine;
N,N-Diethyl-5-[3-(4-fluorophenyl)-3H-imidazo[4,5-c]pyridin-2-yl]pyrimidin-2-amine;
N,N-Diethyl-5-[3-(4-methylphenyl)-3H-imidazo[4,5-c]pyridin-2-yl]pyrimidin-2-amine;
N,N-Diethyl-5-[3-(5-methylpyridin-2-yl)-3H-imidazo[4,5-c]pyridin-2-yl]pyrimidin-2-amine;
4-{5-[3-(2-Fluoro-4-methylphenyl)-3H-imidazo[4,5-c]pyridin-2-yl]-4-methylpyridin-2-yl}morpholine;
4-{5-[3-(4-Chlorophenyl)-3H-imidazo[4,5-c]pyridin-2-yl]-4-methylpyridin-2-yl}morpholine;
5-[3-(4-Methylphenyl)-3H-imidazo[4,5-c]pyridin-2-yl]-N-(oxan-4-yl)pyridin-2-amine;
2-(4,4-Difluoropiperidin-1-yl)-5-[3-(4-methylphenyl)-3H-imidazo[4,5-c]pyridin-2-yl]pyridine;
4-{5-[3-(5-Chloropyridin-2-yl)-3H-imidazo[4,5-c]pyridin-2-yl]-4-methylpyridin-2-yl}morpholine;
4-{4-Methyl-5-[3-(5-methylpyridin-2-yl)-3H-imidazo[4,5-c]pyridin-2-yl]pyridin-2-yl}morpholine;
4-{5-[3-(5-Fluoropyridin-2-yl)-3H-imidazo[4,5-c]pyridin-2-yl]-4-methylpyridin-2-yl}morpholine;
5-[3-(4-Fluorophenyl)-3H-imidazo[4,5-c]pyridin-2-yl]-N-(oxan-4-yl)pyridin-2-amine;
4-{5-[3-(4-Fluorophenyl)-3H-imidazo[4,5-c]pyridin-2-yl]pyridin-2-yl}thiomorpholine;
N-Cyclopropyl-5-[3-(4-methylphenyl)-3H-imidazo[4,5-c]pyridin-2-yl]pyridin-2-amine;
5-[3-(6-Methylpyridin-3-yl)-3H-imidazo[4,5-c]pyridin-2-yl]-2-(pyrrolidin-1-yl)pyridine;
2-(4-Fluoropiperidin-1-yl)-5-[3-(6-methylpyridin-3-yl)-3H-imidazo[4, 5-c]pyridin-2-yl]pyridine;
5-[3-(4-Fluorophenyl)-3H-imidazo[4,5-c]pyridin-2-yl]-N-[2-(morpholin-4-yl)ethyl]pyridin-2-amine;
5-[3-(4-Methylphenyl)-3H-imidazo[4,5-c]pyridin-2-yl]-N-[2-(morpholin-4-yl)ethyl]pyridin-2-amine;
N-Cyclopropyl-5-[3-(4-fluorophenyl)-3H-imidazo[4,5-c]pyridin-2-yl]pyridin-2-amine;
N-Cyclopropyl-5-[3-(6-methylpyridin-3-yl)-3H-imidazo[4,5-c]pyridin-2-yl]pyridin-2-amine;
5-[3-(4-Methylphenyl)-3H-imidazo[4,5-c]pyridin-2-yl]-N-(propan-2-yl)pyridin-2-amine;
5-[3-(6-Methylpyridin-3-yl)-3H-imidazo[4,5-c]pyridin-2-yl]-2-(pyrrolidin-1-yl)pyrimidine;
5-[3-(5-Methylpyridin-2-yl)-3H-imidazo[4,5-c]pyridin-2-yl]-2-(pyrrolidin-1-yl)pyrimidine;
5-[3-(5-Fluoropyridin-2-yl)-3H-imidazo[4,5-c]pyridin-2-yl]-2-(pyrrolidin-1-yl)pyrimidine;
4-{4-[3-(6-Methylpyridin-3-yl)-3H-imidazo[4,5-c]pyridin-2-yl]phenyl}morpholine;
5-[3-(4-Methylphenyl)-3H-imidazo[4,5-c]pyridin-2-yl]-2-(pyrrolidin-1-yl)pyrimidine;
4-{4-[3-(5-Methylpyridin-2-yl)-3H-imidazo[4,5-c]pyridin-2-yl]phenyl}morpholine;
2-Methyl-5-{2-[4-(pyrrolidin-1-yl)phenyl]-3H-imidazo[4,5-c]pyridin-3-yl}pyridine;
5-{2-[2-Fluoro-4-(pyrrolidin-1-yl)phenyl]-3H-imidazo[4,5-c]pyridin-3-yl}-2-methylpyridine;
4-{3-Fluoro-4-[3-(6-methylpyridin-3-yl)-3H-imidazo[4,5-c]pyridin-2-yl]phenyl}morpholine;
5-{2-[3-Fluoro-4-(pyrrolidin-1-yl)phenyl]-3H-imidazo[4,5-c]pyridin-3-yl}-2-methylpyridine;
N-{4-[3-(6-Methylpyridin-3-yl)-3H-imidazo[4,5-c]pyridin-2-yl]phenyl}oxan-4-amine;
5-Methyl-2-{2-[4-(pyrrolidin-1-yl)phenyl]-3H-imidazo[4,5-c]pyridin-3-yl}pyridine;
5-{2-[4-(4-Fluoropiperidin-1-yl)phenyl]-3H-imidazo[4,5-c]pyridin-3-yl}-2-methylpyridine;
2-Chloro-5-[3-(4-chlorophenyl)-3H-imidazo[4,5-c]pyridin-2-yl]pyridine; and
2-Chloro-5-[3-(4-fluorophenyl)-3H-imidazo[4,5-c]pyridin-2-yl]pyridine; or
a pharmaceutically acceptable salt thereof.

2. A pharmaceutical composition comprising:
4-{5-[3-(5-Fluoropyridin-2-yl)-3H-imidazo[4,5-c]pyridin-2-yl]pyridin-2-yl}morpholine;
4-{5-[3-(2,4-Difluorophenyl)-3H-imidazo[4,5-c]pyridin-2-yl]-4-methylpyridin-2-yl}morpholine;
5-[3-(2,4-Difluorophenyl)-3H-imidazo[4,5-c]pyridin-2-yl]-N-(oxan-4-yl)pyrimidin-2-amine;
N,N-Diethyl-5-[3-(6-methylpyridin-3-yl)-3H-imidazo[4,5-c]pyridin-2-yl]pyrimidin-2-amine;
N,N-Diethyl-5-[3-(4-fluorophenyl)-3H-imidazo[4,5-c]pyridin-2-yl]pyrimidin-2-amine;
N,N-Diethyl-5-[3-(4-methylphenyl)-3H-imidazo[4,5-c]pyridin-2-yl]pyrimidin-2-amine;
N,N-Diethyl-5-[3-(5-methylpyridin-2-yl)-3H-imidazo[4,5-c]pyridin-2-yl]pyrimidin-2-amine;
4-{5-[3-(2-Fluoro-4-methylphenyl)-3H-imidazo[4,5-c]pyridin-2-yl]-4-methylpyridin-2-yl}morpholine;
4-{5-[3-(4-Chlorophenyl)-3H-imidazo[4,5-c]pyridin-2-yl]-4-methylpyridin-2-yl}morpholine;
5-[3-(4-Methylphenyl)-3H-imidazo[4,5-c]pyridin-2-yl]-N-(oxan-4-yl)pyridin-2-amine;
2-(4,4-Difluoropiperidin-1-yl)-5-[3-(4-methylphenyl)-3H-imidazo[4,5-c]pyridin-2-yl]pyridine;
4-{5-[3-(5-Chloropyridin-2-yl)-3H-imidazo[4,5-c]pyridin-2-yl]-4-methylpyridin-2-yl}morpholine;
4-{4-Methyl-5-[3-(5-methylpyridin-2-yl)-3H-imidazo[4,5-c]pyridin-2-yl]pyridin-2-yl}morpholine;
4-{5-[3-(5-Fluoropyridin-2-yl)-3H-imidazo[4,5-c]pyridin-2-yl]-4-methylpyridin-2-yl}morpholine;
5-[3-(4-Fluorophenyl)-3H-imidazo[4,5-c]pyridin-2-yl]-N-(oxan-4-yl)pyridin-2-amine;
4-{5-[3-(4-Fluorophenyl)-3H-imidazo[4,5-c]pyridin-2-yl]pyridin-2-yl}thiomorpholine;

N-Cyclopropyl-5-[3-(4-methylphenyl)-3H-imidazo[4,5-c]pyridin-2-yl]pyridin-2-amine;
5-[3-(6-Methylpyridin-3-yl)-3H-imidazo[4,5-c]pyridin-2-yl]-2-(pyrrolidin-1-yl)pyridine;
2-(4-Fluoropiperidin-1-yl)-5-[3-(6-methylpyridin-3-yl)-3H-imidazo[4, 5-c]pyridin-2-yl]pyridine;
5-[3-(4-Fluorophenyl)-3H-imidazo[4,5-c]pyridin-2-yl]-N-[2-(morpholin-4-yl)ethyl]pyridin-2-amine;
5-[3-(4-Methylphenyl)-3H-imidazo[4,5-c]pyridin-2-yl]-N-[2-(morpholin-4-yl)ethyl]pyridin-2-amine;
N-Cyclopropyl-5-[3-(4-fluorophenyl)-3H-imidazo[4,5-c]pyridin-2-yl]pyridin-2-amine;
N-Cyclopropyl-5-[3-(6-methylpyridin-3-yl)-3H-imidazo[4,5-c]pyridin-2-yl]pyridin-2-amine;
5-[3-(4-Methylphenyl)-3H-imidazo[4,5-c]pyridin-2-yl]-N-(propan-2-yl)pyridin-2-amine;
5-[3-(6-Methylpyridin-3-yl)-3H-imidazo[4,5-c]pyridin-2-yl]-2-(pyrrolidin-1-yl)pyrimidine;
5-[3-(5-Methylpyridin-2-yl)-3H-imidazo[4,5-c]pyridin-2-yl]-2-(pyrrolidin-1-yl)pyrimidine;
5-[3-(5-Fluoropyridin-2-yl)-3H-imidazo[4,5-c]pyridin-2-yl]-2-(pyrrolidin-1-yl)pyrimidine;
4-{4-[3-(6-Methylpyridin-3-yl)-3H-imidazo[4,5-c]pyridin-2-yl]phenyl}morpholine;
5-[3-(4-Methylphenyl)-3H-imidazo[4,5-c]pyridin-2-yl]-2-(pyrrolidin-1-yl)pyrimidine;
4-{4-[3-(5-Methylpyridin-2-yl)-3H-imidazo[4,5-c]pyridin-2-yl]phenyl}morpholine;
2-Methyl-5-{2-[4-(pyrrolidin-1-yl)phenyl]-3H-imidazo[4,5-c]pyridin-3-yl}pyridine;
5-{2-[2-Fluoro-4-(pyrrolidin-1-yl)phenyl]-3H-imidazo[4,5-c]pyridin-3-yl}-2-methylpyridine;
4-{3-Fluoro-4-[3-(6-methylpyridin-3-yl)-3H-imidazo[4,5-c]pyridin-2-yl]phenyl}morpholine;
5-{2-[3-Fluoro-4-(pyrrolidin-1-yl)phenyl]-3H-imidazo[4,5-c]pyridin-3-yl}-2-methylpyridine;
N-{4-[3-(6-Methylpyridin-3-yl)-3H-imidazo[4,5-c]pyridin-2-yl]phenyl}oxan-4-amine;
5-Methyl-2-{2-[4-(pyrrolidin-1-yl)phenyl]-3H-imidazo[4,5-c]pyridin-3-yl}pyridine;
5-{2-[4-(4-Fluoropiperidin-1-yl)phenyl]-3H-imidazo[4,5-c]pyridin-3-yl}-2-methylpyridine;
2-Chloro-5-[3-(4-chlorophenyl)-3H-imidazo[4,5-c]pyridin-2-yl]pyridine; and
2-Chloro-5-[3-(4-fluorophenyl)-3H-imidazo[4,5-c]pyridin-2-yl]pyridine; or
a pharmaceutically acceptable salt thereof, together with one or more pharmaceutically acceptable carriers and/or excipients.

3. A method for inhibiting tumor growth in a subject, comprising administering to the subject an effective amount of a compound selected from the group consisting of:
4-{5-[3-(5-Fluoropyridin-2-yl)-3H-imidazo[4,5-c]pyridin-2-yl]pyridin-2-yl}morpholine;
4-{5-[3-(2,4-Difluorophenyl)-3H-imidazo[4,5-c]pyridin-2-yl]-4-methylpyridin-2-yl}morpholine;
5-[3-(2,4-Difluorophenyl)-3H-imidazo[4,5-c]pyridin-2-yl]-N-(oxan-4-yl)pyrimidin-2-amine;
N,N-Diethyl-5-[3-(6-methylpyridin-3-yl)-3H-imidazo[4,5-c]pyridin-2-yl]pyrimidin-2-amine;
N,N-Diethyl-5-[3-(4-fluorophenyl)-3H-imidazo[4,5-c]pyridin-2-yl]pyrimidin-2-amine;
N,N-Diethyl-5-[3-(4-methylphenyl)-3H-imidazo[4,5-c]pyridin-2-yl]pyrimidin-2-amine;
N,N-Diethyl-5-[3-(5-methylpyridin-2-yl)-3H-imidazo[4,5-c]pyridin-2-yl]pyrimidin-2-amine;
4-{5-[3-(2-Fluoro-4-methylphenyl)-3H-imidazo[4,5-c]pyridin-2-yl]-4-methylpyridin-2-yl}morpholine;
4-{5-[3-(4-Chlorophenyl)-3H-imidazo[4,5-c]pyridin-2-yl]-4-methylpyridin-2-yl}morpholine;
5-[3-(4-Methylphenyl)-3H-imidazo[4,5-c]pyridin-2-yl]-N-(oxan-4-yl)pyridin-2-amine;
2-(4,4-Difluoropiperidin-1-yl)-5-[3-(4-methylphenyl)-3H-imidazo[4,5-c]pyridin-2-yl]pyridine;
4-{5-[3-(5-Chloropyridin-2-yl)-3H-imidazo[4,5-c]pyridin-2-yl]-4-methylpyridin-2-yl}morpholine;
4-{4-Methyl-5-[3-(5-methylpyridin-2-yl)-3H-imidazo[4,5-c]pyridin-2-yl]pyridin-2-yl}morpholine;
4-{5-[3-(5-Fluoropyridin-2-yl)-3H-imidazo[4,5-c]pyridin-2-yl]-4-methylpyridin-2-yl}morpholine;
5-[3-(4-Fluorophenyl)-3H-imidazo[4,5-c]pyridin-2-yl]-N-(oxan-4-yl)pyridin-2-amine;
4-{5-[3-(4-Fluorophenyl)-3H-imidazo[4,5-c]pyridin-2-yl]pyridin-2-yl}thiomorpholine;
N-Cyclopropyl-5-[3-(4-methylphenyl)-3H-imidazo[4,5-c]pyridin-2-yl]pyridin-2-amine;
5-[3-(6-Methylpyridin-3-yl)-3H-imidazo[4,5-c]pyridin-2-yl]-2-(pyrrolidin-1-yl)pyridine;
2-(4-Fluoropiperidin-1-yl)-5-[3-(6-methylpyridin-3-yl)-3H-imidazo[4, 5-c]pyridin-2-yl]pyridine;
5-[3-(4-Fluorophenyl)-3H-imidazo[4,5-c]pyridin-2-yl]-N-[2-(morpholin-4-yl)ethyl]pyridin-2-amine;
5-[3-(4-Methylphenyl)-3H-imidazo[4,5-c]pyridin-2-yl]-N-[2-(morpholin-4-yl)ethyl]pyridin-2-amine;
N-Cyclopropyl-5-[3-(4-fluorophenyl)-3H-imidazo[4,5-c]pyridin-2-yl]pyridin-2-amine;
N-Cyclopropyl-5-[3-(6-methylpyridin-3-yl)-3H-imidazo[4,5-c]pyridin-2-yl]pyridin-2-amine;
5-[3-(4-Methylphenyl)-3H-imidazo[4,5-c]pyridin-2-yl]-N-(propan-2-yl)pyridin-2-amine;
5-[3-(6-Methylpyridin-3-yl)-3H-imidazo[4,5-c]pyridin-2-yl]-2-(pyrrolidin-1-yl)pyrimidine;
5-[3-(5-Methylpyridin-2-yl)-3H-imidazo[4,5-c]pyridin-2-yl]-2-(pyrrolidin-1-yl)pyrimidine;
5-[3-(5-Fluoropyridin-2-yl)-3H-imidazo[4,5-c]pyridin-2-yl]-2-(pyrrolidin-1-yl)pyrimidine;
4-{4-[3-(6-Methylpyridin-3-yl)-3H-imidazo[4,5-c]pyridin-2-yl]phenyl}morpholine;
5-[3-(4-Methylphenyl)-3H-imidazo[4,5-c]pyridin-2-yl]-2-(pyrrolidin-1-yl)pyrimidine;
4-{4-[3-(5-Methylpyridin-2-yl)-3H-imidazo[4,5-c]pyridin-2-yl]phenyl}morpholine;
2-Methyl-5-{2-[4-(pyrrolidin-1-yl)phenyl]-3H-imidazo[4,5-c]pyridin-3-yl}pyridine;
5-{2-[2-Fluoro-4-(pyrrolidin-1-yl)phenyl]-3H-imidazo[4,5-c]pyridin-3-yl}-2-methylpyridine;
4-{3-Fluoro-4-[3-(6-methylpyridin-3-yl)-3H-imidazo[4,5-c]pyridin-2-yl]phenyl}morpholine;
5-{2-[3-Fluoro-4-(pyrrolidin-1-yl)phenyl]-3H-imidazo[4,5-c]pyridin-3-yl}-2-methylpyridine;
N-{4-[3-(6-Methylpyridin-3-yl)-3H-imidazo[4,5-c]pyridin-2-yl]phenyl}oxan-4-amine;
5-Methyl-2-{2-[4-(pyrrolidin-1-yl)phenyl]-3H-imidazo[4,5-c]pyridin-3-yl}pyridine;
5-{2-[4-(4-Fluoropiperidin-1-yl)phenyl]-3H-imidazo[4,5-c]pyridin-3-yl}-2-methylpyridine;
2-Chloro-5-[3-(4-chlorophenyl)-3H-imidazo[4,5-c]pyridin-2-yl]pyridine; and
2-Chloro-5-[3-(4-fluorophenyl)-3H-imidazo[4,5-c]pyridin-2-yl]pyridine; or
a pharmaceutically acceptable salt thereof.

4. A method for modulating semicarbazide-sensitive amine oxidase activity in a subject, comprising administering to the subject an effective amount of a compound selected from the group consisting of:

4-{5-[3-(5-Fluoropyridin-2-yl)-3H-imidazo[4,5-c]pyridin-2-yl]pyridin-2-yl}morpholine;
4-{5-[3-(2,4-Difluorophenyl)-3H-imidazo[4,5-c]pyridin-2-yl]-4-methylpyridin-2-yl}morpholine;
5-[3-(2,4-Difluorophenyl)-3H-imidazo[4,5-c]pyridin-2-yl]-N-(oxan-4-yl)pyrimidin-2-amine;
N,N-Diethyl-5-[3-(6-methylpyridin-3-yl)-3H-imidazo[4,5-c]pyridin-2-yl]pyrimidin-2-amine;
N,N-Diethyl-5-[3-(4-fluorophenyl)-3H-imidazo[4,5-c]pyridin-2-yl]pyrimidin-2-amine;
N,N-Diethyl-5-[3-(4-methylphenyl)-3H-imidazo[4,5-c]pyridin-2-yl]pyrimidin-2-amine;
N,N-Diethyl-5-[3-(5-methylpyridin-2-yl)-3H-imidazo[4,5-c]pyridin-2-yl]pyrimidin-2-amine;
4-{5-[3-(2-Fluoro-4-methylphenyl)-3H-imidazo[4,5-c]pyridin-2-yl]-4-methylpyridin-2-yl}morpholine;
4-{5-[3-(4-Chlorophenyl)-3H-imidazo[4,5-c]pyridin-2-yl]-4-methylpyridin-2-yl}morpholine;
5-[3-(4-Methylphenyl)-3H-imidazo[4,5-c]pyridin-2-yl]-N-(oxan-4-yl)pyridin-2-amine;
2-(4,4-Difluoropiperidin-1-yl)-5-[3-(4-methylphenyl)-3H-imidazo[4,5-c]pyridin-2-yl]pyridine;
4-{5-[3-(5-Chloropyridin-2-yl)-3H-imidazo[4,5-c]pyridin-2-yl]-4-methylpyridin-2-yl}morpholine;
4-{4-Methyl-5-[3-(5-methylpyridin-2-yl)-3H-imidazo[4,5-c]pyridin-2-yl]pyridin-2-yl}morpholine;
4-{5-[3-(5-Fluoropyridin-2-yl)-3H-imidazo[4,5-c]pyridin-2-yl]-4-methylpyridin-2-yl}morpholine;
5-[3-(4-Fluorophenyl)-3H-imidazo[4,5-c]pyridin-2-yl]-N-(oxan-4-yl)pyridin-2-amine;
4-{5-[3-(4-Fluorophenyl)-3H-imidazo[4,5-c]pyridin-2-yl]pyridin-2-yl}thiomorpholine;
N-Cyclopropyl-5-[3-(4-methylphenyl)-3H-imidazo[4,5-c]pyridin-2-yl]pyridin-2-amine;
5-[3-(6-Methylpyridin-3-yl)-3H-imidazo[4,5-c]pyridin-2-yl]-2-(pyrrolidin-1-yl)pyridine;
2-(4-Fluoropiperidin-1-yl)-5-[3-(6-methylpyridin-3-yl)-3H-imidazo[4, 5-c]pyridin-2-yl]pyridine;
5-[3-(4-Fluorophenyl)-3H-imidazo[4,5-c]pyridin-2-yl]-N-[2-(morpholin-4-yl)ethyl]pyridin-2-amine;
5-[3-(4-Methylphenyl)-3H-imidazo[4,5-c]pyridin-2-yl]-N-[2-(morpholin-4-yl)ethyl]pyridin-2-amine;
N-Cyclopropyl-5-[3-(4-fluorophenyl)-3H-imidazo[4,5-c]pyridin-2-yl]pyridin-2-amine;
N-Cyclopropyl-5-[3-(6-methylpyridin-3-yl)-3H-imidazo[4,5-c]pyridin-2-yl]pyridin-2-amine;
5-[3-(4-Methylphenyl)-3H-imidazo[4,5-c]pyridin-2-yl]-N-(propan-2-yl)pyridin-2-amine;
5-[3-(6-Methylpyridin-3-yl)-3H-imidazo[4,5-c]pyridin-2-yl]-2-(pyrrolidin-1-yl)pyrimidine;
5-[3-(5-Methylpyridin-2-yl)-3H-imidazo[4,5-c]pyridin-2-yl]-2-(pyrrolidin-1-yl)pyrimidine;
5-[3-(5-Fluoropyridin-2-yl)-3H-imidazo[4,5-c]pyridin-2-yl]-2-(pyrrolidin-1-yl)pyrimidine;
4-{4-[3-(6-Methylpyridin-3-yl)-3H-imidazo[4,5-c]pyridin-2-yl]phenyl}morpholine;
5-[3-(4-Methylphenyl)-3H-imidazo[4,5-c]pyridin-2-yl]-2-(pyrrolidin-1-yl)pyrimidine;
4-{4-[3-(5-Methylpyridin-2-yl)-3H-imidazo[4,5-c]pyridin-2-yl]phenyl}morpholine;
2-Methyl-5-{2-[4-(pyrrolidin-1-yl)phenyl]-3H-imidazo[4,5-c]pyridin-3-yl}pyridine;
5-{2-[2-Fluoro-4-(pyrrolidin-1-yl)phenyl]-3H-imidazo[4,5-c]pyridin-3-yl}-2-methylpyridine;
4-{3-Fluoro-4-[3-(6-methylpyridin-3-yl)-3H-imidazo[4,5-c]pyridin-2-yl]phenyl}morpholine;
5-{2-[3-Fluoro-4-(pyrrolidin-1-yl)phenyl]-3H-imidazo[4,5-c]pyridin-3-yl}-2-methylpyridine;
N-{4-[3-(6-Methylpyridin-3-yl)-3H-imidazo[4,5-c]pyridin-2-yl]phenyl}oxan-4-amine;
5-Methyl-2-{2-[4-(pyrrolidin-1-yl)phenyl]-3H-imidazo[4,5-c]pyridin-3-yl}pyridine;
5-{2-[4-(4-Fluoropiperidin-1-yl)phenyl]-3H-imidazo[4,5-c]pyridin-3-yl}-2-methylpyridine;
2-Chloro-5-[3-(4-chlorophenyl)-3H-imidazo[4,5-c]pyridin-2-yl]pyridine; and
2-Chloro-5-[3-(4-fluorophenyl)-3H-imidazo[4,5-c]pyridin-2-yl]pyridine; or
a pharmaceutically acceptable salt thereof.

5. The method of claim 4, wherein the subject suffers from a disease, condition, or disorder selected from the group consisting of inflammation, an inflammatory disease, an immune disorder and an autoimmune disorder.

6. The method of claim 5, wherein the disease, condition, or disorder is selected from the group consisting of Sjogren's disease, Alzheimer's disease, Parkinson's disease, a pulmonary inflammatory disease, a fibrotic disease, an ischemic disease, an inflammatory disease of the skin, an inflammatory disease of the eye, an inflammatory condition of the liver, an autoimmune condition of the liver, a condition associated with inflammation of the bowel, arthritis, synovitis, vasculitis, atherosclerosis, multiple sclerosis, vascular dementia, systemic inflammatory response syndrome, sepsis, epilepsy, chronic heart failure, congestive heart failure, cerebral amyloid angiopathy, cerebral autosomal dominant arteriopathy with subcortical infarcts and leukoencephalopathy, diabetes, a complication of diabetes, myocardial infarction, and a complication of myocardial infarction.

7. The method of claim 5, wherein the disease, condition, or disorder is selected from the group consisting of Sjogren's disease, Alzheimer's disease, Parkinson's disease, chronic obstructive pulmonary disease, liver fibrosis, inflammatory bowel disease, rheumatoid arthritis, osteoarthritis, multiple sclerosis, and vascular dementia.

8. The method of claim 6, wherein the pulmonary inflammatory disease is selected from the group consisting of asthma, chronic obstructive pulmonary disease, and acute respiratory distress syndrome.

9. The method of claim 6, wherein the fibrotic disease is selected from the group consisting of idiopathic pulmonary fibrosis, cardiac fibrosis, liver fibrosis, systemic sclerosis, and scleroderma.

10. The method of claim 6, wherein the ischemic disease is selected from the group consisting of stroke and ischemia-reperfusion injury.

11. The method of claim 6, wherein the inflammatory disease of the skin is selected from the group consisting of contact dermatitis, atopic dermatitis, and psoriasis.

12. The method of claim 6, wherein the inflammatory disease of the eye is selected from the group consisting of age related macular degeneration, uveitis, and diabetic retinopathy.

13. The method of claim 6, wherein the inflammatory condition of the liver or autoimmune condition of the liver is selected from the group consisting of primary biliary cirrhosis, alcoholic liver disease, sclerosing cholangitis, autoimmune cholangitis, and autoimmune hepatitis.

14. The method of claim 6, wherein the condition associated with inflammation of the bowel is selected from the group consisting of Crohn's disease, ulcerative colitis, inflammatory bowel disease, and irritable bowel syndrome.

15. The method of claim 6, wherein the arthritis is selected from the group consisting of rheumatoid arthritis, osteoarthritis, and psoriatic arthritis.

16. The method of claim 15, wherein the rheumatoid arthritis is juvenile rheumatoid arthritis.

17. The method of claim 6, wherein the diabetes is selected from the group consisting of type I diabetes and type II diabetes.

* * * * *